(12) United States Patent
Thondikulam et al.

(10) Patent No.: US 12,586,682 B1
(45) Date of Patent: Mar. 24, 2026

(54) INTELLIGENT OMNICHANNEL CONVERSATIONAL INTERFACE

(71) Applicant: Kaiser Foundation Hospitals, Oakland, CA (US)

(72) Inventors: Ganesh Thondikulam, Pleasanton, CA (US); Narayanan Gopala, San Diego, CA (US); Pratabkumar Vemana, Marietta, GA (US)

(73) Assignee: KAISER FOUNDATION HOSPITALS, Oakland, CA (US)

( * ) Notice: Subject to any disclaimer, the term of this patent is extended or adjusted under 35 U.S.C. 154(b) by 191 days.

(21) Appl. No.: 18/068,307

(22) Filed: Dec. 19, 2022

Related U.S. Application Data

(60) Provisional application No. 63/291,416, filed on Dec. 19, 2021.

(51) Int. Cl.
| | |
|---|---|
| *G06F 40/40* | (2020.01) |
| *G16H 10/20* | (2018.01) |
| *G16H 40/67* | (2018.01) |
| *G16H 50/20* | (2018.01) |
| *G16H 50/30* | (2018.01) |
| *G16H 80/00* | (2018.01) |

(52) U.S. Cl.
CPC ............ *G16H 40/67* (2018.01); *G06F 40/40* (2020.01); *G16H 10/20* (2018.01); *G16H 50/20* (2018.01); *G16H 50/30* (2018.01); *G16H 80/00* (2018.01)

(58) Field of Classification Search
None
See application file for complete search history.

(56) References Cited

U.S. PATENT DOCUMENTS

| | | | | |
|---|---|---|---|---|
| 6,557,027 | B1 * | 4/2003 | Cragun | H04L 51/04 |
| | | | | 719/329 |
| 11,195,617 | B1 * | 12/2021 | Singh | G16H 50/70 |
| 2001/0043235 | A1 * | 11/2001 | Best | G06F 9/451 |
| | | | | 715/781 |
| 2011/0145757 | A1 * | 6/2011 | Janwari | G06F 3/0485 |
| | | | | 715/802 |
| 2014/0074454 | A1 * | 3/2014 | Brown | G10L 15/08 |
| | | | | 704/235 |
| 2020/0329144 | A1 * | 10/2020 | Morgan | G06F 40/30 |
| 2021/0082311 | A1 * | 3/2021 | Karas | G10L 15/187 |
| 2022/0021630 | A1 * | 1/2022 | Goyal | G06N 3/08 |

* cited by examiner

*Primary Examiner* — Bion A Shelden
(74) *Attorney, Agent, or Firm* — PATENT LAW WORKS LLP

(57) ABSTRACT

An intelligent conversational interface application uses an artificial intelligence platform to provide patient members access to health care. Artificial Intelligence and machine learning (ML) based approaches significantly optimize the patient member's experience and efficiently utilize care coordination and delivery workflows in healthcare organizations. Trained machine learning models are used to determine recommended actions associated with a patient's health condition through the intelligent conversational interface application.

14 Claims, 26 Drawing Sheets

1000

Receive user input from a patient member user through an interactive conversational interface 1002

Determine one or more health conditions associated with the patient member user based on the received user input 1004

Present the determined one or more health conditions and a series of questions related to the one or more health conditions 1006

Receive responses to the series of questions 1008

Determine one or more recommended actions for the patient member user to access health care related to the one or more health conditions based on the received responses using one or more machine learning models 1010

Based on one or more actions performed by the patient member user, generate one or more additional recommended actions 1012

Based on one or more actions performed by the patient member user, train the one or more machine learning models used to generate the one or more recommended actions and the one or more additional recommended actions 1014

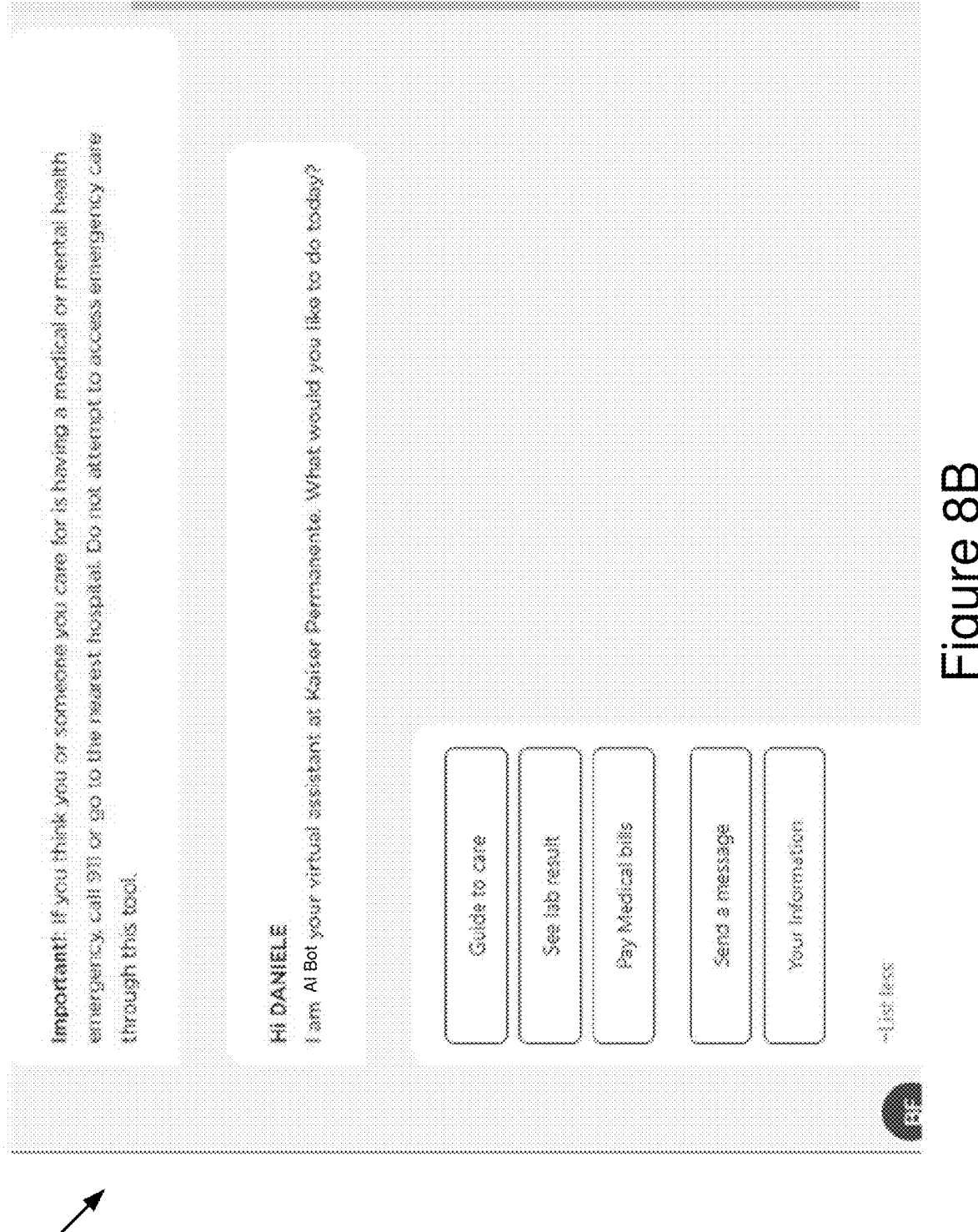

Important: If you think you or someone you care for is having a medical or mental health emergency, call 911 or go to the nearest hospital. Do not attempt to access emergency care through this tool.

Hi DANIELE
I am AI Bot your virtual assistant at Kaiser Permanente. What would you like to do today?

Guide to care

See lab result

Pay Medical bills

Send a message

Your information

Figure 8C:
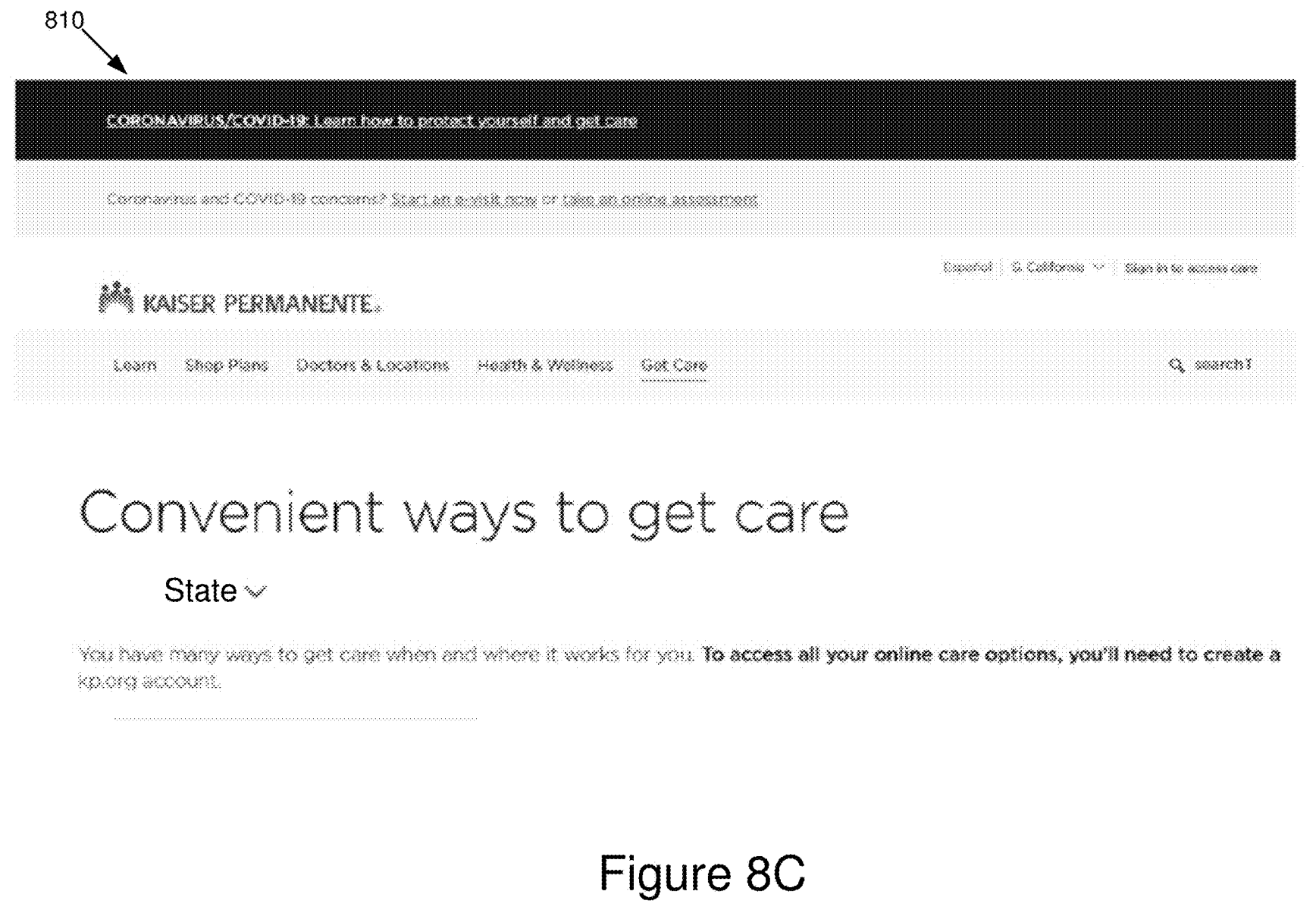

CORONAVIRUS (COVID-19): Learn how to protect yourself and get care

Coronavirus and COVID-19 concerns? Get an e-visit, skip the in-line visit online assessment

KAISER PERMANENTE.

Learn    Shop Plans    Doctors & Locations    Health & Wellness    Get Care

English | U. California ⌄ | Sites as access.com

🔍 search ↑

Convenient ways to get care

State ⌄

You have many many ways to get care when and where it works for you. To access all your online care options, you'll need to create a kp.org account.

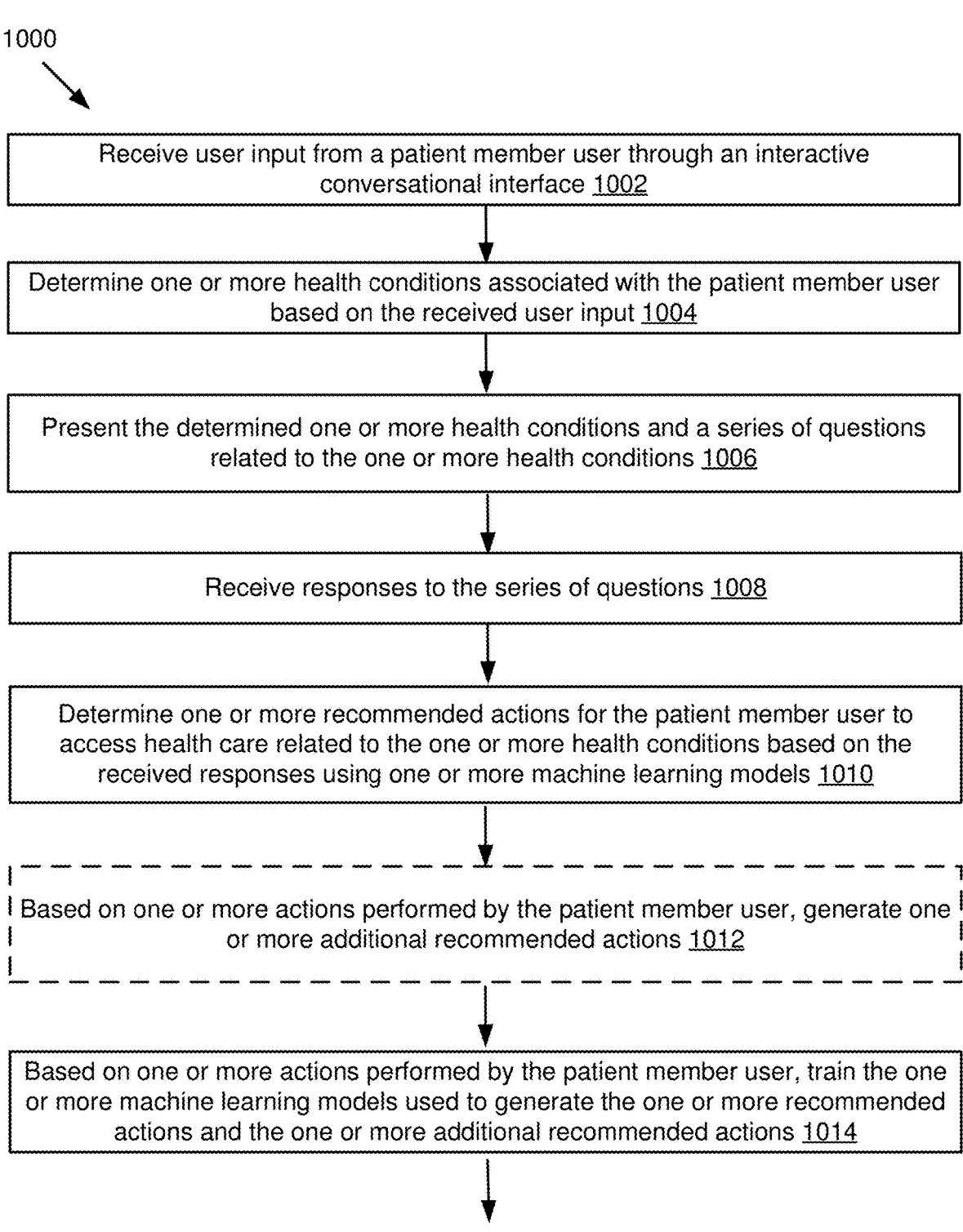

Receive user input from a patient member user through an interactive conversational interface 1002

Determine one or more health conditions associated with the patient member user based on the received user input 1004

Present the determined one or more health conditions and a series of questions related to the one or more health conditions 1006

Receive responses to the series of questions 1008

Determine one or more recommended actions for the patient member user to access health care related to the one or more health conditions based on the received responses using one or more machine learning models 1010

Based on one or more actions performed by the patient member user, generate one or more additional recommended actions 1012

Based on one or more actions performed by the patient member user, train the one or more machine learning models used to generate the one or more recommended actions and the one or more additional recommended actions 1014

Figure 10

INTELLIGENT OMNICHANNEL CONVERSATIONAL INTERFACE

CROSS REFERENCE TO RELATED APPLICATIONS

This application claims the benefit of U.S. Provisional Patent Application No. 63/291,416, titled "Intelligent Omnichannel Conversational Interface," filed Dec. 19, 2022, the entire contents of which are herein incorporated by reference.

BACKGROUND

This specification relates to providing patients with access to care for appropriate healthcare services using an intelligent omnichannel conversational interface. In particular, the specification relates to a system and method for facilitating a patient member with effortless access to healthcare choices using an intelligent omnichannel conversational interface.

Healthcare organizations, healthcare providers, physician offices, and hospitals continuously receive healthcare-related requests from users. Additionally, many users are beginning to interact with these entities via innovative technologies or channels such as via the web, video, online messaging, email, texting, in addition to the more traditional ways of interacting such as telephone or in-person conversations. Several issues arise with so many new and different ways of patient-entity interactions. The interactions are siloed without channel cross-over, limited options and lack of understanding, missed opportunities with human interactions, and an inability to seamlessly transition to another channel. Typically, users must adopt a channel and become familiar with its navigation nuances. Without channel integration and guidance, the users may have to exit and choose a new channel. Furthermore, there is an increasing demand to optimize between the patient waiting times, patient flow, patient preferences, healthcare experience, customer satisfaction, etc. and the efficient utilization of healthcare provider resources, different care coordination and delivery workflows, and health care spending costs.

This background description provided herein is for the purpose of presenting the context of the disclosure.

SUMMARY

The techniques introduced herein overcome the deficiencies and limitations of the prior art, at least in part, with a system and methods for providing patients with access to care for appropriate healthcare services using an intelligent omnichannel conversational interface. In some implementations, the system and methods of the present disclosure uses artificial intelligence (AI) and machine learning (ML) based approaches to significantly optimize between patient member experience and efficient utilization of numerous care coordination and delivery workflows in healthcare organizations. In particular, the system and methods of the present disclosure utilize an omnichannel conversational interface that is backed by trained machine learning and natural language understanding (NLU) models to guide and connect the patient member seeking access to care to various healthcare services without friction. The omnichannel conversational interface is a digital care navigator that serves as a single persona to interact with to receive patient members through different channels or touchpoints of a healthcare organization, personalize the user experience for the patient members, and guide the patient members to perform healthcare services, such as scheduling an appointment, refilling a prescription, connecting the patient member with an appropriate clinical service, etc. Though patient members are facing diverse choices while seeking care, their experience is effortless and not filled with friction as a result of the omnichannel conversational interface.

According to one aspect of the subject matter described in this disclosure, a method includes receiving user input through a conversational interface application; determining one or more health conditions based on the user input; retrieving one or more questions associated with the one or more health conditions; presenting the one or more questions to a patient member user through the conversational interface application; receiving one or more responses to the one or more questions through the conversation interface application; determining one or more recommended actions to access healthcare related to the one or more health conditions based on the one or more responses; and presenting the one or more recommended actions to the patient member user through the conversational interface application.

In general, another aspect of the subject matter described in this disclosure includes a system comprising one or more processors and memory operably coupled with the one or more processors, wherein the memory stores instructions that, in response to execution of the instructions by the one or more processors, cause the one or more processors to perform operations including: receiving user input through a conversational interface application; determining one or more health conditions based on the user input; retrieving one or more questions associated with the one or more health conditions; presenting the one or more questions to a patient member user through the conversational interface application; receiving one or more responses to the one or more questions through the conversation interface application; determining one or more recommended actions to access health care related to the one or more health conditions based on the one or more responses; and presenting the one or more recommended actions to the patient member user through the conversational interface application.

Other implementations of one or more of these aspects include corresponding systems, apparatus, and computer programs, configured to perform the actions of the methods, encoded on computer storage devices.

These and other implementations may each optionally include one or more of the following aspects. For instance, the method further comprising retrieving data related to the patient member user, the data including clinical data about the patient member user; determining a machine learning model based on the clinical data and the data related to the patient member user; and wherein the determining the one or more recommended actions to access the healthcare is also based an output of the machine learning model. In another instance, the method may further include retrieving data related to the patient member user, the data including historical data regarding a health condition; selecting a machine learning model based on the historical data and the data related to the patient member user; and wherein the determining the one or more recommended actions to access the healthcare is based on an output of the machine learning model. For instance, the aspects may also include wherein one or more machine learning models are used in determining the one or more health conditions based on the user input, wherein the one or more machine learning models comprises a trained natural language understanding (NLU) model that classifies user input utterance and one or more of patient member profile, past medical and clinical history, and demographic data. For example, the aspects may also include wherein the one or more machine learning models comprises at least one of a neural network, support vector machine, a decision tree, a Bayesian network, a random decision forest, a k-nearest neighbor, a linear regression, a least squares, and a hidden Markov model. In another example, the aspects may further include that the one or more recommended actions comprises at least one of an in-person office visit, a home visit, a phone call, a video visit, an email, a text, or an instant messaging chat. In still other examples, the conversational interface application includes at least one of a digital interface, a self-service interface, a telephony interface, or an interactive voice response (IVR). For instance, the aspects may also include that determining one or more health conditions based on the user input comprises training specialized bots to orchestrate multiple different requests from the patient member user, the method further comprising prioritizing the multiple different requests based on the one or more health conditions. For example, the aspects may further include that the user input is received based on a history of prior interactions from different engagement channels, and the method further comprises determining the one or more recommended actions based on the history of prior interactions from different engagement channels. In another example, the aspects may further include that method includes receiving feedback from the patient member user completing the one or more recommended actions; and training one or more machine learning models based on the feedback.

The features and advantages described herein are not all-inclusive and many additional features and advantages will be apparent in view of the figures and description. Moreover, it should be understood that the language used in the present disclosure has been principally selected for readability and instructional purposes, and not to limit the scope of the subject matter disclosed herein.

BRIEF DESCRIPTION OF THE DRAWINGS

The disclosure is illustrated by way of example, and not by way of limitation in the figures of the accompanying drawings in which like reference numerals are used to refer to similar elements.

FIGS. 8A-8G are graphical representations of example user interfaces of a patient member accessing the conversational interface for answers to health-related queries.

FIGS. 9A-9K are graphical representations of example user interfaces of a patient member accessing the conversational interface in an appointment booking workflow.

FIG. 10 is an example flowchart diagram of a method of accessing the conversational interface for health-related queries.

DETAILED DESCRIPTION

While the present disclosure may describe the techniques herein in the context of a patient member seeking healthcare services in hospitals, medical clinics and the like, it should be understood that the architecture, principles, and components of the present disclosure may also be used to provide automatic attendant services at a front desk, interactive assistance services in an examination room, pharmaceutical prescription and laboratory test ordering systems, email/messaging with primary care provider (PCP) and care team, interaction with chatbots for medical purposes by patients and medical service providers, screening tool for call center agents, on call questions and analytics, medical condition management application/modules, and interactive voice response (IVR) system using voice analytics. The systems and methods described below may be applied to various other medical care, coordination, and delivery procedures in addition to those specifically set forth below.

Figure 1:
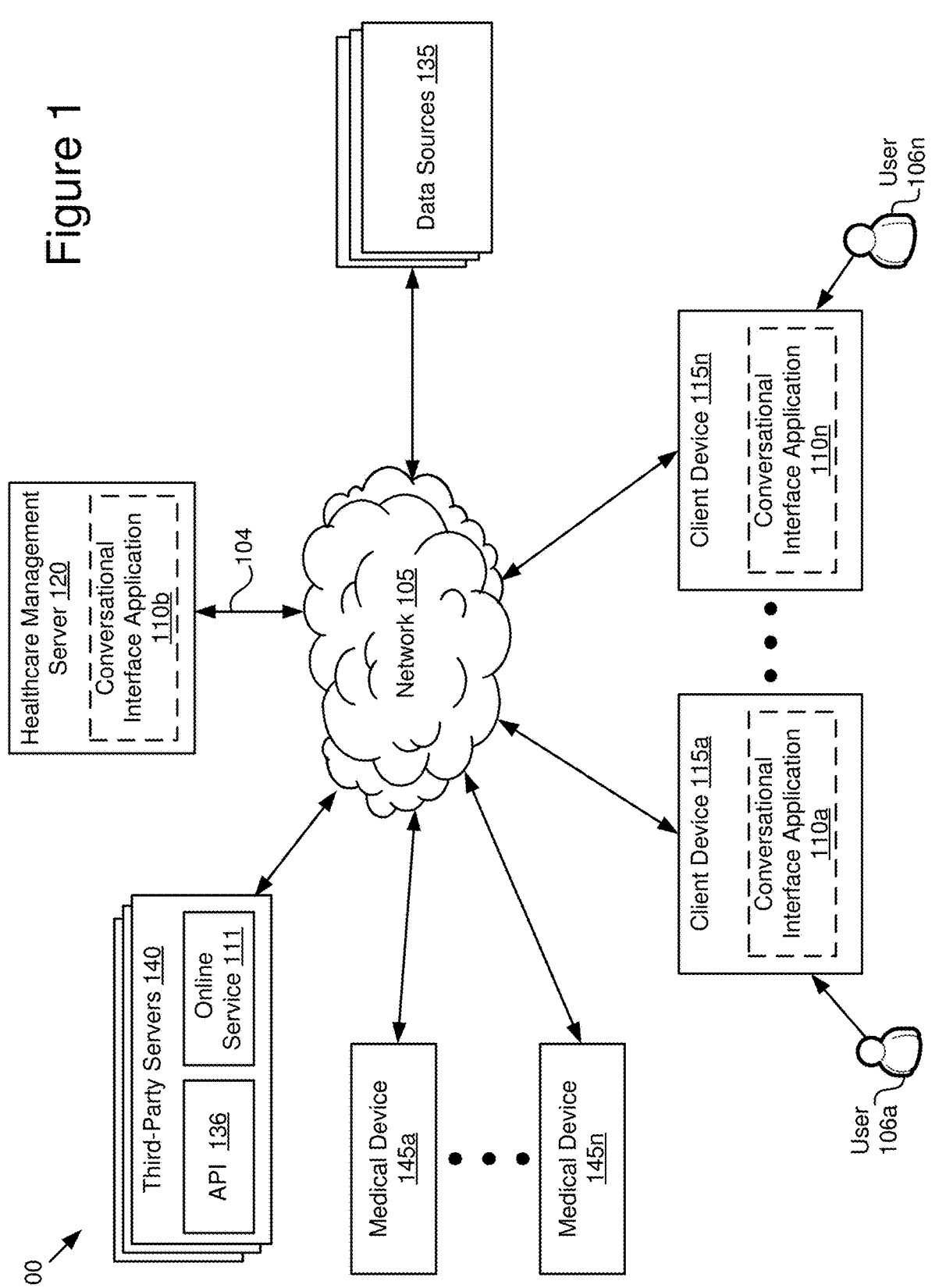
FIG. 1 is a high-level block diagram illustrating one implementation of an example system for providing patients with access to care for appropriate healthcare services using an intelligent omnichannel conversational interface.

FIG. 1 is a high-level block diagram illustrating one implementation of an example system 100 for providing patients with access to care for appropriate healthcare services using an intelligent omnichannel conversational interface. The illustrated system 100 may include one or more client devices 115a . . . 115n that can be accessed by users, a healthcare management server 120, a plurality of data sources 135, a plurality of third-party servers 140, and one or more medical devices 145a . . . 145n which are communicatively coupled via a network 105 for interaction and electronic communication with one another. In FIG. 1 and the remaining figures, a letter after a reference number, e.g., "115a," represents a reference to the element having that particular reference number. A reference number in the text without a following letter, e.g., "115," represents a general reference to instances of the element bearing that reference number The network 105 may be a conventional type, wired or wireless, and may have numerous different configurations including a star configuration, token ring configuration, or other configurations. Furthermore, the network 105 may include any number of networks and/or network types. For example, the network 105 may include a local area network (LAN), a wide area network (WAN) (e.g., the Internet), virtual private networks (VPNs), mobile (cellular) networks, wireless wide area network (WWANs), WiMAX® networks, Bluetooth® communication networks, peer-to-peer networks, near field networks (e.g., NFC, etc.), and/or other interconnected data paths across which multiple devices may communicate, various combinations thereof, etc. The network 105 may also be coupled to or include portions of a telecommunications network for sending data in a variety of different communication protocols. In some implementations, the network 105 may include Bluetooth communication networks or a cellular communications network for sending and receiving data including via short messaging service (SMS), multimedia messaging service (MMS), hypertext transfer protocol (HTTP), direct data connection, WAP, email, etc. In some implementations, the data transmitted by the network 105 may include packetized data (e.g., Internet Protocol (IP) data packets) that is routed to designated computing devices coupled to the network 105. Although FIG. 1 illustrates one network 105 coupled to the client devices 115, the healthcare management server 120, the plurality of data sources 135, the plurality of third-party servers 140, and the medical devices 145, in practice one or more networks 105 can be connected to these entities.

The client devices 115a . . . 115n (also referred to individually and collectively as 115) may be computing devices having data processing and communication capabilities. In some implementations, a client device 115 may include a memory, a processor (e.g., virtual, physical, etc.), a power source, a network interface, software and/or hardware components, such as a display, graphics processing unit (GPU), wireless transceivers, keyboard, camera (e.g., webcam), sensors, firmware, operating systems, web browsers, applications, drivers, and various physical connection interfaces (e.g., USB, HDMI, etc.). The client devices 115a . . . 115n may couple to and communicate with one another and the other entities of the system 100 via the network 105 using a wireless and/or wired connection. Examples of client devices 115 may include, but are not limited to, laptops, desktops, tablets, mobile phones (e.g., smartphones, feature phones, etc.), server appliances, servers, virtual machines, smart TVs, media streaming devices, user wearable computing devices (e.g., fitness trackers, etc.) or any other electronic device capable of accessing a network 105. In the example of FIG. 1, the client device 115a is configured to implement a conversational interface application 110a described in more detail below. The client device 115 includes a display for viewing information provided by one or more entities coupled to the network 105. For example, the client device 115 may be adapted to send and receive data to and from the healthcare management server 120. While two or more client devices 115 are depicted in FIG. 1, the system 100 may include any number of client devices 115. In addition, the client devices 115a . . . 115n may be the same or different types of computing devices. The client devices 115a . . . 115n may be associated with the users 106a . . . 106n. For example, users 106a . . . 106n may include patient members, physicians, clinical staff, laboratory technicians, pharmacy technicians, administrative staff, call center agents, etc. of a health care organization. Each client device 115 may be associated with a data channel, such as a mobile application running on a user's smartphone, a computer in a doctor's office, a health tracking device, etc. These data channels may collect data related to one or more users and provide that data to the entities coupled to the network 105. In some implementations, the client devices 115 may be implemented as a computing device 200 as will be described below with reference to FIG. 2.

The medical devices 145a . . . 145n may include, but are not limited to, a stethoscope, a blood pressure meter, a pulse oximeter, a thermometer, an ophthalmoscope, a weight and height scale, an otoscope, a camera, a telecardiology device (e.g. an ECG machine), a telepathology device (e.g. a microscope), a teledermatology device (e.g. a high-resolution camera), a teleradiology device (e.g. an ultrasound machine), a medical radiography equipment (e.g., MRI machine, CT machine, X-ray machine, etc.), etc. associated with one or more health care organizations. Authorized personnel who are trained to use the medical device 145 may obtain the patient's medical information. For example, the authorized personnel may include physicians and clinical staff. In some implementations, the medical device 145 may cooperate with the client device 115 to allow authorized personnel to communicate with other entities of the system 100. For example, the client device 115 receives a report associated with a patient including a medical test result from the medical device 145 and sends the report to the healthcare management server 120 for storage and analysis.

In the example of FIG. 1, the healthcare management server 120, the plurality of data sources 135, and the plurality of the third-party servers 140 may be, or may be implemented by, a computing device including a processor, a memory, applications, a database, and network communication capabilities similar to that described below with reference to FIG. 2.

In the example of FIG. 1, the healthcare management server 120 may be configured to implement a conversational interface application 110b. In some implementations, the healthcare management server 120 may be a hardware server, a software server, or a combination of software and hardware. For example, the healthcare management server 120 may include one or more hardware servers, virtual servers, server arrays, storage devices and/or systems, etc., and/or may be centralized or distributed/cloud based. In some implementations, the healthcare management server 120 may include one or more virtual servers, which operate in a host server environment and access the physical hardware of the host server including, for example, a processor, a memory, applications, a database, storage, network interfaces, etc., via an abstraction layer (e.g., a virtual machine manager). In some implementations, the healthcare management server 120 may be a Hypertext Transfer Protocol (HTTP) server, a Representational State Transfer (REST) service, or other server type, having structure and/or functionality for processing and satisfying content requests and/or receiving content from one or more of the client devices 115, one or more of the medical devices 145, the plurality of data sources 135, and the plurality of third-party servers 140 that are coupled to the network 105.

Also, instead of or in addition, the healthcare management server 120 may implement its own application programming interface (API) for the transmission of instructions, data, results, and other information between the server 120 and other entities communicatively coupled to the network 105. For example, the API may be a software interface exposed over the HTTP protocol by the healthcare management server 120. The API exposes internal data and functionality of the service hosted by the healthcare management server 120 to API requests originating from one or more of the conversational interface applications 110, the plurality of data sources 135, and the plurality of third-party servers 140. In one example, the conversational interface application 110b implemented by the healthcare management server 120 passes an authenticated request including a set of parameters for information to one or more of the third-party servers 140 and the data source 135 and receives an object (e.g., XML or JSON) with associated results. In some implementations, the healthcare management server 120 may also include a database coupled to it (e.g., over the network 105) to store structured data in a relational database and a file system (e.g., HDFS, NFS, etc.) for unstructured or semi-structured data. In some implementations, the healthcare management server 120 may include an instance of a data store that stores various types of data for access and/or retrieval by the conversational interface application 110. For example, the data store may store machine learning models for natural language understanding of user intents. Other types of user data are also possible and contemplated.

In some implementations, the healthcare management server 120 sends and receives data to and from other entities of the system 100 via the network 105. For example, the healthcare management server 120 sends and receives data including instructions to and from the client device 115. In some implementations, the healthcare management server 120 may serve as a middle layer and permit interactions between the client device 115 and the plurality of the third-party servers 140 and the data sources 135 to flow through and from the healthcare management server 120 for security and convenience. In some implementations, the healthcare management server 120 may be operable to receive an appointment request, process the appointment request based on the user context and hospital resource availability, and recommend an appointment modality for treating a patient health condition, etc. The healthcare management server 120 may send data to and receive data from the other entities of the system 100 via the network 105. It should be understood that the healthcare management server 120 is not limited to providing the above-noted acts and/or functionality and may include other network-accessible services. In addition, while a single healthcare management server 120 is depicted in FIG. 1, it should be understood that there may be any number of healthcare management servers 120 or a server cluster.

Each of the one or more third-party servers 140 may be, or may be implemented by, a computing device including a processor, a memory, applications, a database, and network communication capabilities. A third-party server 140 may be a Hypertext Transfer Protocol (HTTP) server, a Representational State Transfer (REST) service, or other server type, having structure and/or functionality for processing and satisfying content requests and/or requesting and receiving content from one or more of the client devices 115, the medical devices 145, the data sources 135, and the healthcare management server 120 that are coupled to the network 105. In some implementations, the third-party server 140 may include an online service 111 dedicated to providing access to various services and information resources hosted by the third-party server 140 via web, mobile, enterprise, and/or cloud applications. The online service 111 may obtain and store user data, user-generated data, content items (e.g., videos, text, images, etc.), and interaction data reflecting the interaction of users with the content items. In some implementations, the third-party server 140 may provide an API 136 to facilitate access of the third-party server 140 by one or more of the client devices 115, the medical devices 145, the data sources 135, and the healthcare management server 120 that are coupled to the network 105. User-generated data, as described herein, may include one or more of user profile information (e.g., user id, user preferences, user history, social network connections, primary care physicians, etc.), logged information (e.g., heart rate, activity metrics, sleep quality data, calories and nutrient data, user device specific information, historical actions, medication history, etc.), and other user specific information. In some implementations, the online service 111 allows users to share content with other users (e.g., friends, contacts, public, similar users, primary care physicians, clinical staff, administrative staff, etc.), purchase and/or view items (e.g., e-books, videos, music, games, subscription, fitness products, prescription refill, laboratory results, etc.), and other similar actions. For example, the online service 111 may provide various services such as digital fitness content; personal training; running and cycling tracking service; music streaming service; mobile health (mHealth) service; video streaming service; web mapping service; multimedia messaging service; electronic mail service; a calendar service; news service; news aggregator service; social networking service; location-based service; photo and video-sharing social networking service; sleep-tracking service; diet-tracking and calorie counting service; ridesharing service; online banking service; online information database service; travel service; online e-commerce marketplace; ratings and review service; restaurant-reservation service; food delivery service; search service; health and fitness service; home automation and security service; Internet of Things (IOT), multimedia hosting, distribution, and sharing service; cloud-based data storage and sharing service; a scheduling service; an enterprise clinical workflow service; a combination of one or more of the foregoing services; or any other service where users retrieve, collaborate, and/or share information, etc. It should be noted that the list of items provided above as examples for the online service 111 above are not exhaustive and that others are contemplated in the techniques described herein.

Each of the plurality of data sources 135 may be, or may be implemented by, a computing device including a processor, a memory, applications, a database, and network communication capabilities. In some implementations, the data sources may be a data warehouse, a system of record (SOR), or belonging to a data repository owned by an organization that provides real-time or close to real-time data automatically or responsive to being polled or queried by the healthcare management server 120. Each of the plurality of data sources 135 may be associated with a first-party entity (e.g., server 120) or third-party entity (e.g., server 140 associated with a separate company or service provider), such as a health insurance organization, a health care organization, world health organization, an independent healthcare provider, a healthcare-related call center or customer service company, a healthcare software company, an Electronic Medical Record (EMR) software company, an Electronic Health Record (EHR) software company, a pharmacy management system, a drug research institute, a patient management software system, a clinical decision support system, a clinical workflow management system, a scheduling system, a patient-satisfaction measurement firm, a medication adherence tracking system, a public-records database, a data mining platform, a Software as a Service (SaaS) data analytics company, a data science and machine learning platform, news site, support groups, health blogs, etc. Examples of data provided by the plurality of data sources 135 may include, but is not limited to, pharmacy data, physician-patient encounter data, clinical data, patient data, EMR, EHR, patient diagnosis data, patient procedures, appointment notes, socioeconomic data, social determinant data, demographic data, health plan data, prescription data, call center data, appointment schedule data, disposition data, calendar data, medication data, pharmaceutical data, survey data, medication adherence data, machine learning models, machine learning-based data analysis results, etc. In some implementations, each of the plurality of data sources 135 may be configured to provide or facilitate an API (not shown) that allows the conversational interface application 110 to access data and information for performing the functionality described herein.

The conversational interface application 110 may include software and/or logic to provide the functionality for providing patients with access to care for appropriate healthcare services using an intelligent omnichannel conversational interface. In some implementations, the conversational interface application 110 may be implemented using programmable or specialized hardware, such as a field-programmable gate array (FPGA) or an application-specific integrated circuit (ASIC). In some implementations, the conversational interface application 110 may be implemented using a combination of hardware and software. In one implementation, the conversational interface application 110*b* is stored and executed on healthcare management server 120 alone. In another implementation, the conversational interface application 110*a*, 110*n* is stored and executed on client device 115 alone. In other implementations, the conversational interface application 110 may be stored and executed on various combinations of the medical devices 145, the client device 115, the data sources 135, the third-party servers 140, and the healthcare management server 120, or by any one of the medical devices 145, the client devices 115, the data sources 135, the third-party servers 140, or the healthcare management server 120.

In some implementations, the conversational interface application 110*a* may be a thin-client application with some functionality executed on the client device 115 and additional functionality executed on the healthcare management server 120 by the conversational interface application 110*b*. In some implementations, the conversational interface application 110 may generate and present various user interfaces to perform these acts and/or functionality, which may in some cases be based at least in part on information received from the healthcare management server 120, the client device 115, the medical device 145, one or more of the third-party servers 140 and/or the data sources 135 via the network 105. In some implementations, the conversational interface application 110 is code operable in a web browser, a web application accessible via a web browser, a native application (e.g., mobile application, installed application, etc.) on the client device 115, a combination thereof, etc. Additional structure, acts, and/or functionality of the conversational interface application 110 is further discussed below with reference to at least FIG. 2.

In some implementations, the conversational interface application 110 may require users to be registered with the healthcare management server 120 to access the acts and/or functionality described herein. For example, to access various acts and/or functionality provided by the conversational interface application 110, the conversational interface application 110 may require a user to authenticate his/her identity. For example, the conversational interface application 110 may require a user seeking access to authenticate their identity by inputting credentials in an associated user interface. In another example, the conversational interface application 110 may interact with a federated identity server (not shown) to register and/or authenticate the user by scanning and verifying biometrics including username and password, facial attributes, fingerprint, and voice.

Other variations and/or combinations are also possible and contemplated. It should be understood that the system 100 illustrated in FIG. 1 is representative of an example system and that a variety of different system environments and configurations are contemplated and are within the scope of the present disclosure. For example, various acts and/or functionality may be moved from a server 120 to a client device 115, or vice versa, data may be consolidated into a single data store or further segmented into additional data stores, and some implementations may include additional or fewer computing devices, services, and/or networks, and may implement various functionality client or server-side. Furthermore, various entities of the system may be integrated into a single computing device or system or divided into additional computing devices or systems, etc.

Figure 2:
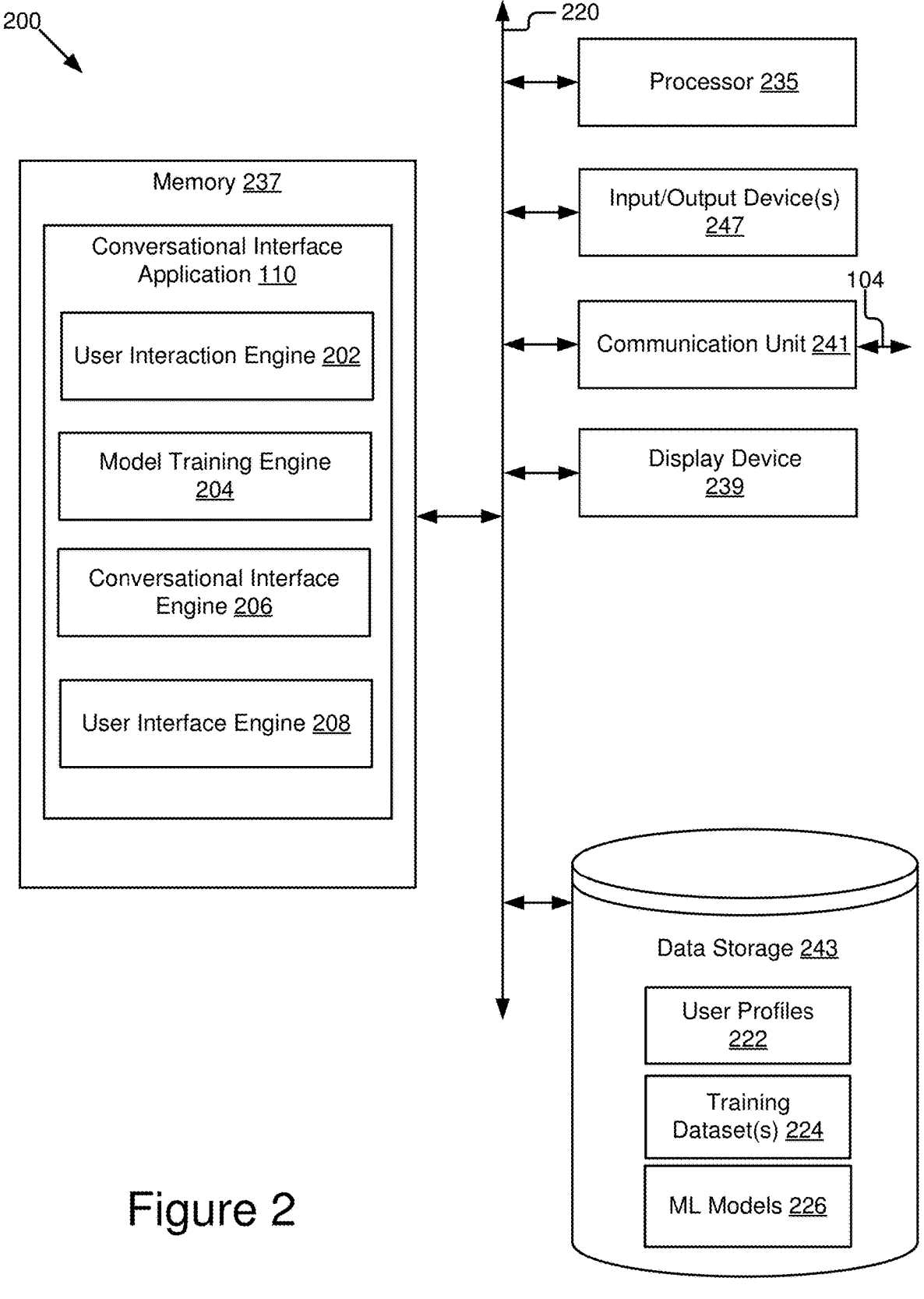
FIG. 2 is a block diagram illustrating one implementation of a computing device including a conversational interface application.

FIG. 2 is a block diagram illustrating one implementation of a computing device 200 including a conversational interface application 110. The computing device 200 may also include a processor 235, a memory 237, a display device 239, a communication unit 241, an input/output device(s) 247, and a data storage 243, according to some examples. The components of the computing device 200 are communicatively coupled by a bus 220. In some implementations, the computing device 200 may be representative of the client device 115, the healthcare management server 120, or a combination of the client device 115 and the healthcare management server 120. In such implementations where the computing device 200 is the client device 115 or the healthcare management server 120, it should be understood that the client device 115 and the healthcare management server 120 may take other forms and include additional or fewer components without departing from the scope of the present disclosure. For example, while not shown, the computing device 200 may include sensors, capture devices, additional processors, and other physical configurations. Additionally, it should be understood that the computer architecture depicted in FIG. 2 could be applied to other entities of the system 100 with various modifications, including, for example, the servers 140 and data sources 135.

The processor 235 may execute software instructions by performing various input/output, logical, and/or mathematical operations. The processor 235 may have various computing architectures to process data signals including, for example, a complex instruction set computer (CISC) architecture, a reduced instruction set computer (RISC) architecture, and/or an architecture implementing a combination of instruction sets. The processor 235 may be physical and/or virtual, and may include a single processing unit or a plurality of processing units and/or cores. In some implementations, the processor 235 may be capable of generating and providing electronic display signals to a display device 239, supporting the display of images, capturing and transmitting images, and performing complex tasks including various types of feature extraction and sampling. In some implementations, the processor 235 may be coupled to the memory 237 via the bus 220 to access data and instructions therefrom and store data therein. The bus 220 may couple the processor 235 to the other components of the computing device 200 including, for example, the memory 237, the communication unit 241, the display device 239, the input/output device(s) 247, and the data storage 243.

The memory 237 may store and provide access to data for the other components of the computing device 200. The memory 237 may be included in a single computing device or distributed among a plurality of computing devices as discussed elsewhere herein. In some implementations, the memory 237 may store instructions and/or data that may be executed by the processor 235. The instructions and/or data may include code for performing the techniques described herein. For example, as depicted in FIG. 2, the memory 237 may store the conversational interface application 110. The memory 237 is also capable of storing other instructions and data, including, for example, an operating system, hardware drivers, other software applications, databases, etc. The memory 237 may be coupled to the bus 220 for communication with the processor 235 and the other components of the computing device 200.

The memory 237 may include one or more non-transitory computer-usable (e.g., readable, writeable) device, a static random access memory (SRAM) device, a dynamic random access memory (DRAM) device, an embedded memory device, a discrete memory device (e.g., a PROM, FPROM, ROM), a hard disk drive, an optical disk drive (CD, DVD, Blu-ray™, etc.) mediums, which can be any tangible apparatus or device that can contain, store, communicate, or transport instructions, data, computer programs, software, code, routines, etc., for processing by or in connection with the processor 235. In some implementations, the memory 237 may include one or more of volatile memory and non-volatile memory. It should be understood that the memory 237 may be a single device or may include multiple types of devices and configurations.

The bus 220 may represent one or more buses including an industry standard architecture (ISA) bus, a peripheral component interconnect (PCI) bus, a universal serial bus (USB), or some other bus providing similar functionality. The bus 220 may include a communication bus for transferring data between components of the computing device 200 or between computing device 200 and other components of the system 100 via the network 105 or portions thereof, a processor mesh, a combination thereof, etc. In some implementations, the conversational interface application 110 and various other software operating on the computing device 200 (e.g., an operating system, device drivers, etc.) may cooperate and communicate via a software communication mechanism implemented in association with the bus 220. The software communication mechanism may include and/or facilitate, for example, inter-process communication, local function or procedure calls, remote procedure calls, an object broker (e.g., CORBA), direct socket communication (e.g., TCP/IP sockets) among software modules, UDP broadcasts and receipts, HTTP connections, etc. Further, any or all of the communication may be configured to be secure (e.g., SSH, HTTPS, etc.).

The display device 239 may be any conventional display device, monitor or screen, including but not limited to, a liquid crystal display (LCD), light emitting diode (LED), organic light-emitting diode (OLED) display or any other similarly equipped display device, screen, or monitor. The display device 239 represents any device equipped to display user interfaces, electronic images, and data as described herein. In some implementations, the display device 239 may output display in binary (only two different values for pixels), monochrome (multiple shades of one color), or multiple colors and shades. The display device 239 is coupled to the bus 220 for communication with the processor 235 and the other components of the computing device 200. In some implementations, the display device 239 may be a touch-screen display device capable of receiving input from one or more fingers of a user. For example, the display device 239 may be a capacitive touch-screen display device capable of detecting and interpreting multiple points of contact with the display surface. In some implementations, the computing device 200 (e.g., client device 115) may include a graphics adapter (not shown) for rendering and outputting the images and data for presentation on display device 239. The graphics adapter (not shown) may be a separate processing device including a separate processor and memory (not shown) or may be integrated with the processor 235 and memory 237.

The input/output (I/O) device(s) 247 may include any standard device for inputting or outputting information and may be coupled to the computing device 200 either directly or through intervening I/O controllers. In some implementations, the input device 247 may include one or more peripheral devices. Non-limiting example I/O devices 247 include a touch screen or any other similarly equipped display device equipped to display user interfaces, electronic images, and data as described herein, a touchpad, a keyboard, a scanner, a stylus, an audio reproduction device (e.g., speaker), a microphone array, a barcode reader, an eye gaze tracker, a sip-and-puff device, and any other I/O components for facilitating communication and/or interaction with users. In some implementations, the functionality of the input/output device 247 and the display device 239 may be integrated, and a user of the computing device 200 (e.g., client device 115) may interact with the computing device 200 by contacting a surface of the display device 239 using one or more fingers. For example, the user may interact with an emulated (i.e., virtual, or soft) keyboard displayed on the touch-screen display device 239 by using fingers to contact the display in the keyboard regions.

The communication unit 241 is hardware for receiving and transmitting data by linking the processor 235 to the network 105 and other processing systems via signal line 104. The communication unit 241 receives data such as requests from the client device 115 and transmits the requests to the conversational interface application 110, for example a request to schedule an appointment with a healthcare provider. The communication unit 241 also transmits information including media to the client device 115 for display, for example, in response to the request. The communication unit 241 is coupled to the bus 220. In some implementations, the communication unit 241 may include a port for direct physical connection to the client device 115 or to another communication channel. For example, the communication unit 241 may include an RJ45 port or similar port for wired communication with the client device 115. In other implementations, the communication unit 241 may include a wireless transceiver (not shown) for exchanging data with the client device 115 or any other communication channel using one or more wireless communication methods, such as IEEE 802.11, IEEE 802.16, Bluetooth® or another suitable wireless communication method.

In yet other implementations, the communication unit 241 may include a cellular communications transceiver for sending and receiving data over a cellular communications network such as via short messaging service (SMS), multimedia messaging service (MMS), hypertext transfer protocol (HTTP), direct data connection, WAP, e-mail or another suitable type of electronic communication. In still other implementations, the communication unit 241 may include a wired port and a wireless transceiver. The communication unit 241 also provides other conventional connections to the network 105 for distribution of files and/or media objects using standard network protocols such as TCP/IP, HTTP, HTTPS, and SMTP as will be understood to those skilled in the art.

The data storage 243 is a non-transitory memory that stores data for providing the functionality described herein. In some implementations, the data storage 243 may be coupled to the components 235, 237, 239, 241, 243, and 247 via the bus 220 to receive and provide access to data. In some implementations, the data storage 243 may store data received from other elements of the system 100 including, for example, entities 135, 140, 145, and/or the conversational interface applications 110, and may provide data access to these entities. The data storage 243 may store, among other data, user profiles 222, training datasets 224, and machine learning models 226. The data stored in the data storage 243 is described below in more detail.

The data storage 243 may be included in the computing device 200 or in another computing device and/or storage system distinct from but coupled to or accessible by the computing device 200. The data storage 243 may include one or more non-transitory computer-readable mediums for storing the data. In some implementations, the data storage 243 may be incorporated with the memory 237 or may be distinct therefrom. The data storage 243 may be a dynamic random-access memory (DRAM) device, a static random-access memory (SRAM) device, flash memory, or some other memory devices. In some implementations, the data storage 243 may include a database management system (DBMS) operable on the computing device 200. For example, the DBMS could include a structured query language (SQL) DBMS, a NoSQL DMBS, various combinations thereof, etc. In some instances, the DBMS may store data in multi-dimensional tables comprised of rows and columns, and manipulate, e.g., insert, query, update and/or delete, rows of data using programmatic operations. In other implementations, the data storage 243 also may include a non-volatile memory or similar permanent storage device and media including a hard disk drive, a CD-ROM device, a DVD-ROM device, a DVD-RAM device, a DVD-RW device, a flash memory device, or some other mass storage device for storing information on a more permanent basis.

It should be understood that other processors, operating systems, sensors, displays, and physical configurations are possible.

As depicted in FIG. 2, the memory 237 may include the conversational interface application 110. In some implementations, the conversational interface application 110 may be configured to implement a secure HTTP API (not shown) to facilitate web, mobile, enterprise, and/or cloud applications for providing patients with access to care for appropriate healthcare services using an intelligent omnichannel conversational interface.

In some implementations, the conversational interface application 110 may include a user interaction engine 202, a model training engine 204, a conversational interface engine 206, and a user interface engine 208. The components 202, 204, 206, and 208 may be communicatively coupled by the bus 220 and/or the processor 235 to one another and/or the other components 237, 239, 241, 243, and 247 of the computing device 200 for cooperation and communication. The components 202, 204, 206, and 208 may each include software and/or logic to provide their respective functionality. In some implementations, the components 202, 204, 206, and 208 may each be implemented using programmable or specialized hardware including a field-programmable gate array (FPGA) or an application-specific integrated circuit (ASIC). In some implementations, the components 202, 204, 206, and 208 may each be implemented using a combination of hardware and software executable by the processor 235. In some implementations, each one of the components 202, 204, 206, and 208 may be sets of instructions stored in the memory 237 and configured to be accessible and executable by the processor 235 to provide their acts and/or functionality. In some implementations, the components 202, 204, 206, and 208 may send and receive data, via the communication unit 241, to and from one or more of the client devices 115, the medical devices 145, the healthcare management server 120, the data sources 135, and third-party servers 140.

The user interaction engine 202 may include software and/or logic to provide functionality for receiving, processing, and storing a stream of user data including interaction data aggregated from one or more entities of the system 100. The data may correspond to numerous patient care coordination and delivery systems, such as enterprise clinical and business workflow systems. For example, the data may correspond to a plurality of users, such as patient members, physicians, clinical staff, administrative staff, subject matter experts, call center agents, etc. at one or more of health care organizations. In some implementations, the user interaction engine 202 determines a history of the user interaction data of patient members on different engagement channels (e.g., website, mobile application, phone call, text, interactive voice response (IVR), etc.) seeking access to healthcare from one or more healthcare organizations. For example, the user interaction engine 202 collects interaction data including patient information (e.g., name, age group, gender, location, etc.), reasons for appointment (e.g., symptoms, etc.), time context (e.g., time of day when appointment was requested, day of week when appointment was requested, etc.), questions that were asked during the interaction and answers provided to the same, member preferences (e.g., past appointment choices, etc.), an engagement channel (e.g., website, mobile application, phone call, text, etc.) through which the member interacted, etc.), channel switching (e.g., switching from phone call to video call, switching from mobile application to phone call, etc.) etc. The user interaction engine 202 is coupled to the data storage 243 to store the data in the data storage 243.

In some implementations, the user interaction engine 202 receives a stream of health or clinical data and retail pharmacy data associated with the plurality of users. For example, the user interaction engine 202 may query the plurality of data sources 135 for collecting the clinical data and the retail pharmacy data. Clinical data may include, but is not limited to, EMR data, EHR data, patient-physician encounter data (e.g., name, age, phone number, temperature, pulse, weight, height, encounter date, encounter type, encounter reason, encounter location, encounter time, encounter notes, etc.), patient demographics (e.g., gender, birth date, address, preferred language, ethnicity, marital status, religion, etc.), zip-code level demographics data, individual social determinant data (e.g., financial information, education level, mobility, race, alcohol use, tobacco use, drug use, etc.), patient surveys, patient problem list, patient procedures (e.g., ICD procedure codes, procedure date, procedure results, etc.), physician appointment history, upcoming appointment data, patient diagnoses, medical laboratory test results data, hospitalization data, rehabilitation data, health plan data, Center for Medicare & Medicaid Services Hierarchical Condition Category (CMS-HCC) risk score, census data and other public data (e.g., geography-level), etc. Pharmacy data may include, but is not limited to, prescription data, medication data (e.g., medication ID, date ordered, start and end date, etc.), pharmaceutical data, medication history, medication refills (e.g., number of refills, etc.), medication adherence data, proportion of days covered (PDC) score, polypharmacy data, drug interaction data, drug dosage, etc. The user interaction engine 202 processes, correlates, integrates, and synchronizes the received data streams from disparate devices 115, 145, servers 140, and data sources 135 into a consolidated data stream to perform the functionalities as described herein. For example, the user interaction engine 202 links the enterprise clinical and business workflow data obtained in association with a patient member (e.g., tracked through user identifier, triage session, etc.) to the user interaction data for context and personalization of healthcare.

In some implementations, the user interaction engine 202 instantiates a data ingestion layer that transports data from assorted data sources 135 to data storage 243 where it can be stored, accessed, and analyzed by the conversational interface application 110. For example, the data ingestion layer processes incoming data, prioritizes sources, validates individual files, and routes the data to the data storage 243. In some implementations, the user interaction engine 202 instantiates a data transformation layer that maps and converts data from a source format (e.g., of a data source 135) to a destination format. For example, the data transformation layer transforms non-XML data to XML data. The user interaction engine 202 creates a user profile 222 for a patient member based on processing the received data streams. The user profile 222 may include data and insights about the user including name, unique user identifier, age, gender, interests, height, weight, risk score, location, profile photo, recently measured vital signs, diagnosed conditions (e.g., diabetic, mental health, heart attack, etc.), medical history, user preferences (e.g., phone call for upcoming reminders, etc.), appointment preferences (e.g., video call for virtual urgent care visits, etc.), prescription (e.g., refill dates, etc.), laboratory test results, treatment or care plans, fitness goals (e.g., gain physical mobility, lose weight, etc.), activities (e.g. number of physical therapy sessions, number of missed appointments, synced wearable fitness devices, synced third-party mobile Health applications, etc.), etc. The user interaction engine 202 stores and updates the user profiles 222 in the data storage 243.

The model training engine 204 may include software and/or logic to provide functionality for generating training datasets 224 and training one or more machine learning models 226 or classifiers using the training datasets 224. In some implementations, the model training engine 204 curates one or more training datasets 224 based on the data received and processed in association with a plurality of the client devices 115, the medical devices 145, the third-party servers 140, and the data sources 135. For example, the model training engine 204 receives the healthcare-related call center data, cleans the call center data, and derives sample historical and curated text or speech utterance data (words, phrases, sentences, etc.) for generating the training datasets 224. Example training datasets 224 curated by the model training engine 204 may include, but not limited to, a dataset containing utterances of historical multilingual user input with a labelled health or urgent disease condition as output to predict, a dataset of health condition identification hints and patterns, a dataset of appointment booking data for different scripts or reasons for appointment (e.g., rash, physical exam, flu, etc.), a dataset of appointment booking data for different modalities of appointment (e.g., video call, phone call, in-person visit, text-based urgent care, etc.), a dataset of appointment booking data for patient members of different age groups (e.g., 0-18, 18-45, 45-65, 65+), a dataset of appointment booking data for patient members of different demographics, a dataset of patient member profiles and patient dispositions for the member profiles, a dataset of medical dictionary terms and indexed search terms, a dataset of patient member profiles and appointment modality of recent bookings for the member profiles, a dataset of clinical context (e.g., past and current health conditions, medications, allergies, laboratory results, treatments, historical encounter data, current encounter data, etc.) for a number of patient members, etc. In some implementations, the model training engine 204 may create a crowdsourced training dataset 224. For example, in the instance where a user (e.g., patient member) consents to use of their data for creating a training dataset, the model training engine 204 forwards the aggregated data to remotely located reviewers to review the data, identify a segment of the data, classify and provide a label for the identified data segment. The model training engine 204 stores the curated training datasets 224 in the data storage 243. The model training engine 204 uses the training datasets 224 to train the machine learning models for performing the various functionality as described herein. The model training engine 204 stores the trained machine learning models 226 in the data storage 243.

The model training engine 204 creates one or more machine learning models 226 for the conversational interface engine 206 (described in detail below) to identify intent based on user input. For example, the machine learning model 226 may be a trained natural language understanding (NLU) model that is able to classify user input utterance (e.g., text or speech) and one or more of patient member profile, past medical and clinical history, user interaction history on different channels, demographic data, etc. to identify intent of a red flag health condition (e.g., with a classification score) of a patient member, intent to schedule, reschedule or cancel an appointment, intent to refill a medical prescription, patient validation, status check, referral, information retrieval, COVID screening, location, leave a message for a primary care physician, etc. The model training engine 204 generates one or more machine learning models 226 for supporting multi-lingual input classification. For example, the NLU models may be trained to be native language-specific and extended to support multi-lingual user inputs in English, Spanish, Vietnamese, Russian, etc. In another example, the model training engine 204 generates machine learning models 226 for performing language translation of user inputs. In yet another example, the model training engine 204 uses a combination of language-specific models and language translation models.

The model training engine 204 facilitates providing input necessary to create a particular machine learning model 226. In some implementations, the model training engine 204 receives and/or generates data, models, training data, and scoring parameters necessary to create the machine learning model 226. For example, the model training engine 204 may provide curated multilingual text inputs, provide health condition identification hints and patterns, provide model negators, perform training, testing, approve, and publish model versions for consumption, perform scoring model parameter tuning, or create scoring accuracy thresholds for generating a model. The model training engine 204 is adapted to receive input from users, such as data scientists, analysts, or operational staff at virtual medical center to define and enhance the machine learning models 226. For example, the operational staff may increase or decrease weights for different intent recognitions in the retraining of the machine learning models 226. The model training engine 204 may provide a secure portal through which these users may define, train, test, publish, refine, and improve the machine learning models 226 or introduce new models. For example, the portal may be used to define, train, test and publish NLU models for identification of different intents. In another example, the portal may be used to define, train, test and publish models for recommendation of an appointment modality for a healthcare appointment sought by a patient member. The portal allows the users to provide training data—text inputs or spoken word utterances, multi-lingual input, synonyms, conjugation, typos, mispronunciations, model negators, etc. The portal enables the users to define and modify scoring thresholds. The portal allows users to enhance the models during training using machine learning hints, patterns, and/or phrases. The portal further enables the users to control or reduce the overlap of inputs between classes during the training of a machine learning model.

In some implementations, the model training engine 204 emphasizes certain sets of features, traits, or attributes in a machine learning model during hyperparameter tuning for improving recognition, accuracy, computational speed, etc. For example, NLU models may be trained based on the following features or attributes, including but not limited to: patient member profile (age, gender, location, race, socio-economic, etc.); patient member clinical context (e.g., past and current health conditions, medications, allergies, labo-ratory results, treatments, historical encounter data, current encounter data, etc.); medical terms and dictionary; or statistics of input text, predicted disease conditions, pro-posed and actual dispositions. In some implementations, the model training engine 204 augments or enhances the NLU model with a knowledge base that includes a medical dictionary, index search terms and associated dispositions for those terms. The knowledge base may also be enhanced to include data such as text input matches to text input frequency, disease frequency, drift between prediction and actual disposition, disease severity, patient member profile (e.g., age, gender, location, language, and other demo-graphic data, etc.), physician or subject matter expert inputs. The model training engine 204 provides the machine models 226 to the data storage 243 for storage.

The model training engine 204 facilitates developing and providing a screening questionnaire in association with an identified intent of a patient member during a patient care and coordination workflow. For example, the screening questionnaire is presented as a digital intervention during an appointment booking workflow. Through extensive clinical domain knowledge and analysis, screening questionnaires are developed for each applicable intent of the patient member. The model training engine 204 provides a portal for users with clinical domain knowledge and expertise to define, refine, author, optimize, and promote screening ques-tionnaires as digital intervention for each applicable intent. For example, the portal may be used for authoring of questions and ordering of questions; approving and publish-ing of questionnaire versions; enable demographics-based filtering (e.g., define filters based on member demographics) of screening questionnaire; enable medical condition-based filtering (e.g., define filters based on member medical his-tory) of screening questionnaire, configure thresholds for surfacing the screening questionnaire in association with an identified health condition, etc. In another example, the screening questionnaire may be developed for an urgent (e.g., "red flag") disease or health condition, booking an appointment, information retrieval, medication refill, etc. The model training engine 204 creates one or more machine learning models for the conversational interface engine 206 (described in detail below) to identify and surface screening questionnaire in association with identified intents. The model training engine 204 provides the screening question-naire to the data storage 243 for storage.

In some implementations, the model training engine 204 may be configured to incrementally adapt and train the one or more machine learning models 226 every threshold period of time. For example, the model training engine 204 may incrementally train the machine learning models 226 every hour, every day, every week, every month, etc. based on the aggregated dataset and feedback data generated based on prior predictions made by the machine learning models 226. In some implementations, a machine learning model 226 is a neural network model and includes a layer and/or layers of memory units where memory units each have corresponding weights. A variety of neural network models may be utilized including feed forward neural networks, convolutional neural networks (CNN), recurrent neural net-works, radial basis functions, other neural network models, as well as combinations of several neural networks. Addi-tionally, the machine learning model 226 may represent a variety of other machine learning techniques in addition to neural networks, for example, support vector machines, decision trees, Bayesian networks, random decision forests, k-nearest neighbors, linear regression, least squares, hidden Markov models, other machine learning techniques, and/or combinations of machine learning techniques.

In some implementations, the model training engine 204 may train the machine learning model 226 using any one of at least one of supervised learning (e.g., support vector machines, neural networks, logistic regression, linear regres-sion, stacking, gradient boosting, etc.), unsupervised learn-ing (e.g., clustering, neural networks, singular value decom-position, principal component analysis, etc.), or semi-supervised learning (e.g., generative models, transductive support vector machines, etc.). Additionally, or alternatively, the model training engine 204 may train the machine learn-ing model 226 using tensor networks. For example, the model training engine 204 may mine the database to build links across the objects, such as patient members and their preferences, treatments, outcomes, etc. based on features or attributes that they share with each other in order to train the machine learning models 226.

In some implementations, the model training engine 204 uses keyword-based database lookups, or search by key-words and clinical terms to implement training of one or more machine learning models 226. For example, the model training engine 204 may use keyword extraction for unsu-pervised training of classification of user input. In some implementations, the model training engine 204 may use transformers and open-source library frameworks for natural language processing, such as spaCy and Spark NLP to build machine learning algorithms to improve intent identification from user input. In some implementations, the model train-ing engine 204 may train one or more machine learning models 226 to perform a single machine learning task or a variety of machine learning tasks. In other implementations, the machine learning model 226 may be trained to perform multiple tasks. In yet other implementations, the model training engine 204 may train a machine learning model 226 to receive the requested data and generate the response data.

The model training engine 204 determines a plurality of training instances or samples from the training dataset 224. The model training engine 204 may apply a training instance as input to a machine learning model 226. The model training engine 204 may generate a predicted machine learning model output by applying training input to the machine learning model 226. Additionally, or alternatively, the model training engine 204 may compare the predicted machine learning model output with a known labelled output from the training instance and, using the comparison, update one or more weights in the machine learning model 226. In some implementations, the model training engine 204 may update the one or more weights by backpropagating the difference over the entire machine learning model 226.

In some implementations, the model training engine 204 may test a trained machine learning model 226 and update it accordingly. The model training engine 204 may partition the training dataset 224 into a testing dataset and a training dataset. The model training engine 204 may apply a testing instance from the training dataset 224 as input to the trained machine learning model 226. A predicted output generated by applying a testing instance to the trained machine learn-ing model 226 may be compared with a known output for the testing instance to update an accuracy value (e.g., an accu-racy percentage) for the machine learning model 226. In some implementations, the model training engine 204 may version and service the model 226 through an internal HTTP endpoint to be used by other component(s) of the conversational interface application 110. For example, once a model 226 is trained and tested and determined to have acceptable accuracy (e.g., accuracy score satisfying a threshold), the model training engine 204 pushes the model 226 to the conversational interface engine 206 for consumption. In some implementations, model development is an iterative process with retraining, testing, and publishing steps performed iteratively, and adapted automatically to improve scores and accuracy. New versions will be published based on improvements and retraining using historical data and efficiency calculations as more data (e.g., feedback) is collected over a period of time. For example, the NLU model or classifier class labels (disease conditions to be identified) requires clinical and business oversight and will be promoted for usage by capability based on clinical and business review. Continuous retraining using training data (utterances, phrases, hints, negators, language variants, etc.) are performed based on curation as part of clinical and data analysis.

Figure 3:
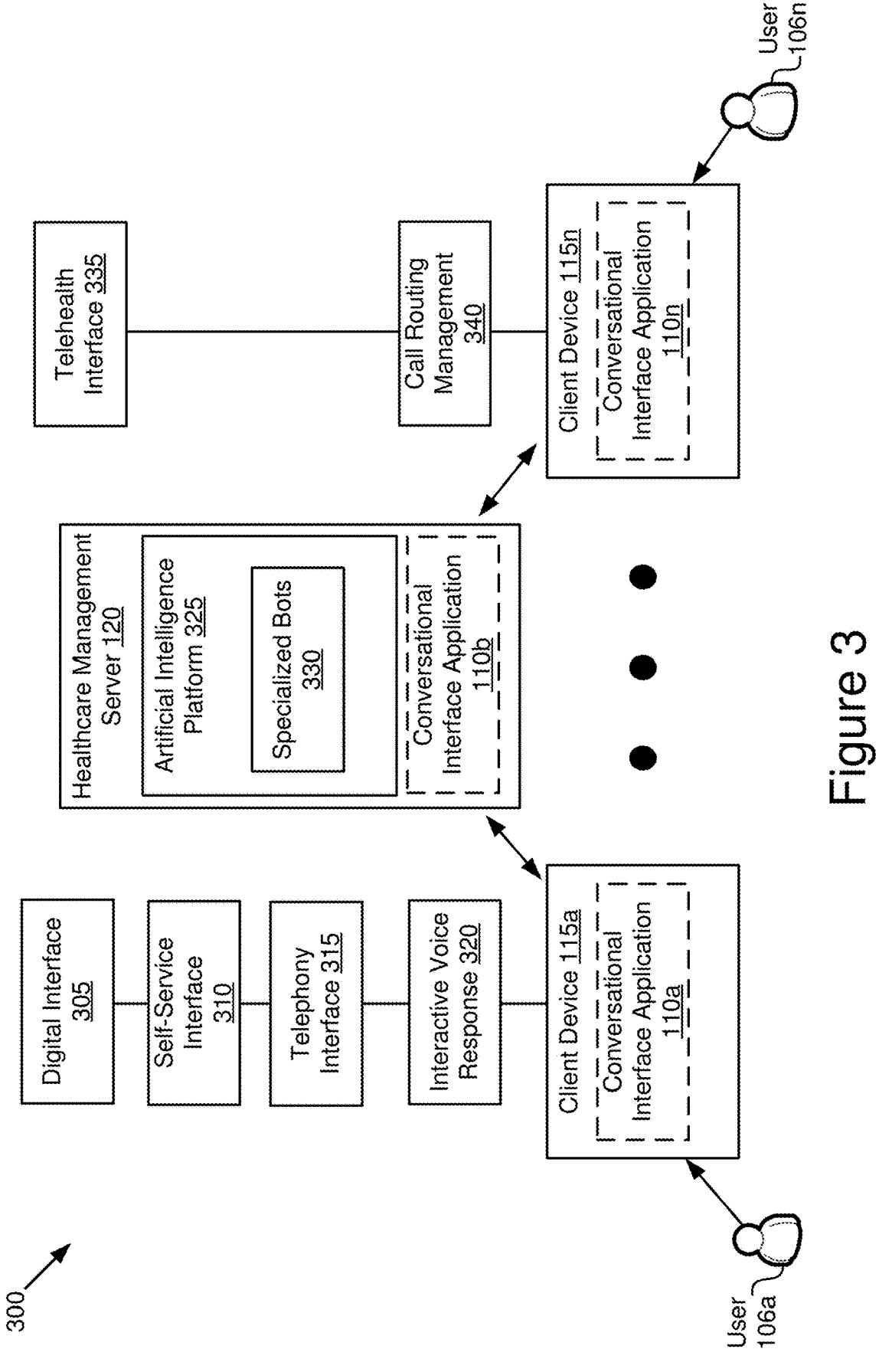
FIG. 3 is a high-level block diagram illustrating a graphical representation of omnichannel integration of a conversational interface.

The conversational interface engine 206 may include software and/or logic to provide functionality for providing a conversational interface and seamlessly connecting patient members on one or more engagement channels to appropriate healthcare services. For example, the engagement channels may include a website, a mobile application, a phone call, interactive voice response (IVR), instant messaging chat, email, etc. In some implementations, the conversational interface engine 206 may be communicatively coupled to instances of multiple engagement channels for performing the functionalities as described herein. FIG. 3 is a high-level block diagram illustrating an example representation 300 of omnichannel integration of a conversational interface. As shown in FIG. 3, the conversational interface is connected to the different engagement channels (e.g., digital interface 305, self-service interface 310, telephony interface 315, interactive voice response (IVR) 320, etc.) used by the members and the different healthcare related services (e.g., call routing management 340, telehealth interface 335, etc.) through which one or more of the agent and health care providers provide care to the patient members. As illustrated, patient members may be users 106 of client devices 115 operating a conversational interface application 110. Similarly, agents and health care providers may also be users 106 of client devices 115 operating a conversational interface application 110. The omnichannel integration of the conversational interface is backed by the artificial intelligence platform 325 operating on the healthcare management server 120. In some implementation, the artificial intelligence platform 325 includes specialized bots 330 that may be generated, over time, based on various needs. For example, a specialized bot 330 may be generated to orchestrate multiple different requests from a patient member user (e.g., sore throat and need to refill prescription). As another example, a specialized bot 330 may be generated to handle a specific health condition or disease (e.g., new COVID-19 booster vaccine availability).

The conversational interface engine 206 identifies a patient member on an engagement channel requesting digital health care and determines a contextual state of the patient member based on their history of prior interactions across different engagement channels. For example, a patient member may have requested a prescription refill via a phone call with a call center agent a day before. When the patient member engages for digital care via instant messaging chat the next day, the conversational interface engine 206 is contextually aware that the patient member requested a recent prescription refill. The conversational interface engine 206 receives user input in association with a patient member on one or more engagement channels. For example, the user input may be received in association with an online booking of an appointment for a patient member with a health care provider during a care coordination delivery workflow. The user input may be one or more of text, speech, voice to text, image, and video. For example, the user input may be providing a reason for visit including symptom entered by the patient member during the online booking of the appointment. The conversational interface engine 206 provides support for multi-lingual user input. In some implementations, the conversational interface engine 206 receives a stream of conversational text and/or speech for stream processing. In other implementations, the conversational interface engine 206 receives a batch of conversational text and/or speech for batch processing. The conversational interface engine 206 performs real time speech to text translation and text to speech translation using one or more of language models, transcription models, and voice recognition models.

Figure 4:
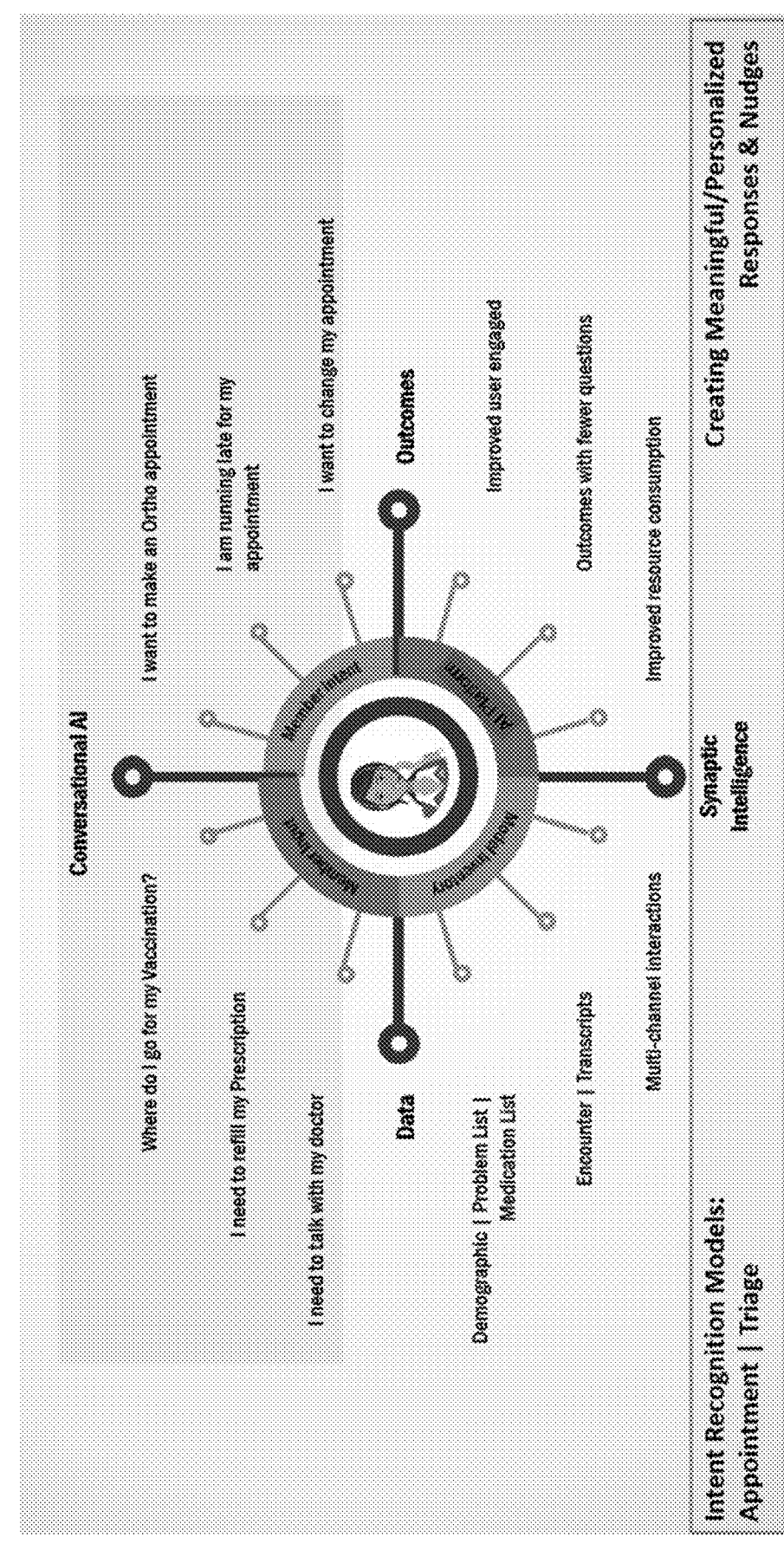
FIG. 4 depicts a graphical representation of an omnichannel conversational interface processing a combination of user input and patient member data to identify intent using machine learning models for delivering improved outcomes in the healthcare of the patient member.

The conversational interface engine 206 is coupled to receive one or more operational machine learning models 226 deployed by the model training engine 204 for identifying intent in the user input, surfacing questionnaire and processing answers to invoke linked healthcare services for the patient member. The conversational interface engine 206 provides natural language understanding of intent based on user input. The conversational interface engine 206 processes the user input using one or more machine learning models 226 (e.g., NLU models) to understand natural language (e.g., English, Spanish, German, etc.) of the user input (e.g., textual words or phrases) and identify the intent (e.g., potential health or disease condition). In addition to the user input, the conversational interface engine 206 may receive and process profile data (e.g., age, gender, demographic data, etc.), clinical data (e.g., past medical history, EHR, etc.), pharmacy data (e.g., medication adherence, etc.) of the patient member using the machine learning model. For example, during the online booking of an appointment, if a patient member indicates they are experiencing dizziness, the conversational interface engine 206 interprets the member's natural language with a NLU model to infer the patient's condition is a red flag condition requiring immediate care based on the member's demographic profile and medical history. FIG. 4 depicts a graphical representation 400 of an omnichannel conversational interface processing a combination of user input and patient member data to identify intent using machine learning models for delivering improved outcomes in the healthcare of the patient member.

The conversational interface engine 206 may be configured to implement a NLU and machine learning-based scoring pipeline for performing text classification and entity recognition on the user input. The conversational interface engine 206 analyzes user input to determine its meaning using one or more NLU models. For example, the NLU model may be a custom model trained for input classification (e.g., intent recognition) and entity recognition using historical call center dataset and medical dictionary terms for health condition identification. In another example, the NLU model may be a machine learning-based service to process natural language understanding via cloud computing. The conversational interface engine 206 recognizes the meaning of the user input by identifying the user's sentiment in the user input and determining their objective. The conversational interface engine 206 identifies the entities in the user input and extracts important information about those entities. For example, the conversational interface engine 206 breaks down a user input "throwing up blood at home" and identifies "vomiting" as intent or health condition and "home" location as entity. In some implementations, the conversational interface engine 206 may modify or adjust the classification score for text classification and intent recognition based on weighting several features associated with the patient member. For example, the conversational interface engine 206 may adjust the classification score based on weighting one or more the following features: patient member profile and demographic data (e.g., age, gender, etc.); patient member's past medical history (e.g., known medical conditions, medications, laboratory and imaging results, etc.); patient's recent and current healthcare appointments, physician encounters and visit data; location; language; language skills (e.g., limited English proficiency); time of medical events (e.g., recent and current events); disease severity; disease frequency; utterance frequency; drift between past disposition predictions and actual dispositions; or various other features. The conversational interface engine 206 further modifies the score based on relevance hints and rules as provided by physicians and other clinical staff (e.g., based on clinical and regulatory requirements) to provide a final output score.

The conversational interface engine 206 surfaces or generates questionnaire based on the identified intent and processes the answers to the questionnaire to invoke appropriate healthcare services or bots. The conversational interface engine 206 directs or routes the patient member to the appropriate healthcare services through the engagement channel in which the patient member requested for care. In some implementations, the conversational interface engine 206 facilitates channel switching for a patient member based on their preference. For example, a patient member initially engaging through an instant messaging chat may be seamlessly switched to a phone call to consult with a live nurse for patient care. All the context of the patient member seeking care is made readily available to the live nurse when the engagement channel is switched for the patient member.

Figure 5:
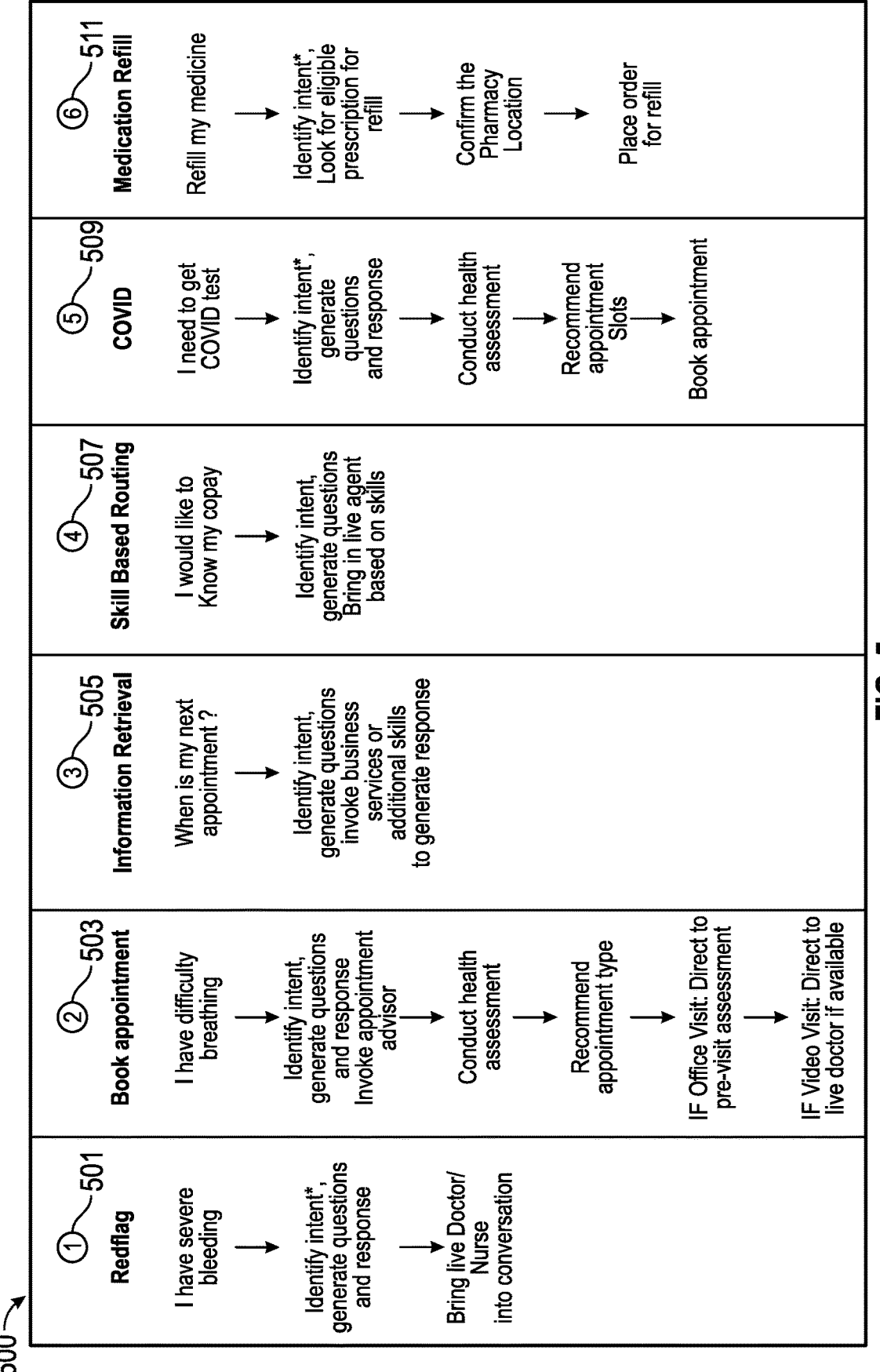
FIG. 5 depicts a graphical representation describing example use cases of intent recognition and connecting the patient member to different healthcare services.

FIG. 5 depicts a graphical representation 500 describing example use cases of intent recognition and connecting the patient member to different healthcare services. In FIG. 5, for the use case "red flag" 501, the conversational interface engine 206 processes the user input "I have severe bleeding" to identify intent of red flag condition for the patient member, generates questionnaire and receives response to bring a live doctor or nurse into the conversation with the patient member. For the use case "book appointment" 503, the conversational interface engine 206 processes the user input "I have difficulty breathing" to identify intent of the patient member wanting to book an appointment and invokes an appointment advisor healthcare service. The appointment advisor healthcare service conducts health assessment and recommends an appointment type. If the appointment type is office visit, the patient member is directed to pre-visit assessment. If the appointment type is video visit, the patient member is directed to a live doctor based on availability. For the use case "information retrieval" 506, the conversational interface engine 206 processes the user input "when is my next appointment" to identify intent of the patient member to get information on their upcoming appointment and invokes an appointment service to generate a response. For the use case "skill-based routing" 507, the conversational interface engine 206 processes the user input "I would like to know my copay" to identify intent of the patient member to wanting to know an answer to a billing or insurance question. The conversational interface engine 206 brings in a call center agent based on the patient member's question and response into the conversation. For the use case "COVID" 509, the conversational interface engine 206 processes the user input "I need to get COVID test" to identify intent of the patient member experiencing COVID-19 symptoms and invoke a health assessment service or bot to assess the symptoms and an appointment booking service or bot to recommend appointment slots for booking. For the use case "medication refill" 511, the conversational interface engine 206 processes the user input "Refill my medicine" to identify intent of the patient member wanting to refill their prescription. The conversational interface engine 206 invokes a refill service to identify an eligible prescription, generate questions and receive response confirming the prescription and the pharmacy location, and place order for refill.

Figure 6:
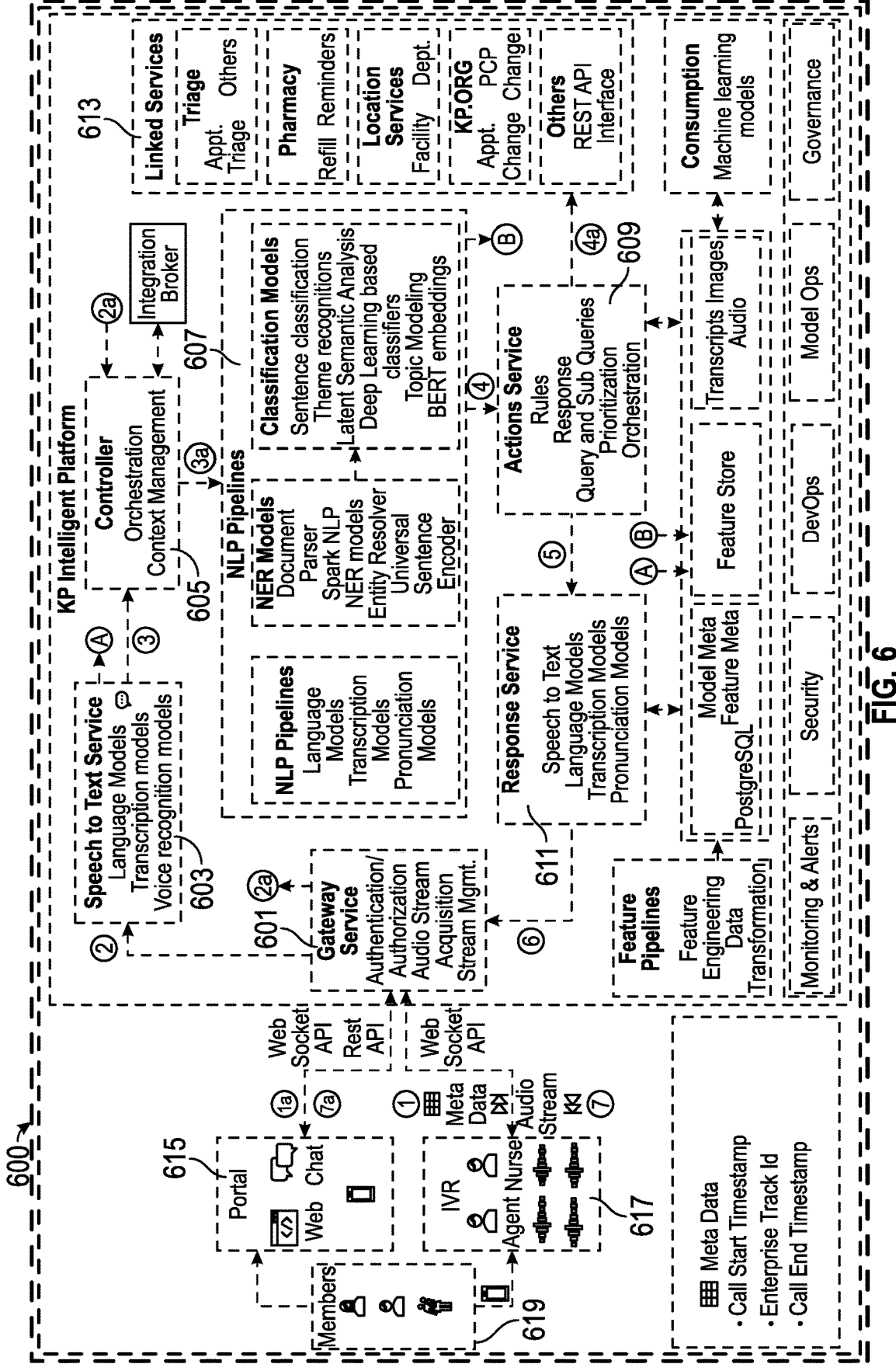
FIG. 6 is a block diagram illustrating an example implementation of an intelligent omnichannel conversational interface.

FIG. 6 is a block diagram 600 illustrating an example implementation of an intelligent omnichannel conversational interface. The gateway service 601 receives the user input from members 619 through the portal 615 including website, instant messaging chat, phone call, or through IVR 617. If the user input is an audio stream or speech, the gateway service 601 engages a speech to text service 603 to convert user input into text. The converted text is sent to the controller 605 which determines the context of the user input and forwards the converted text and context to the NLP pipelines 607 for natural language understanding of user intent. NLP pipelines 607 includes language models, transcription models, pronunciation models. Additionally, NLP pipelines 607 may include number, edition error and recognition error (NER) models and classification models. For example, NER models may include a document parser, Spark NLP NER models, entity resolver, and a universal sentence encoder. Classification models may include sentence classification, theme recognitions, latent semantic analysis, deep learning based classifiers, topic modeling, and Bidirectional Encoder Representations from Transformers (BERT) embeddings. In an implementation, the controller 605 may also orchestrate multiple requests in the user input and generate multiple action threads. The actions service 609 uses the intent to connect the patient member to linked service 613. The actions service 609 also generates a query to present to the member and receive response for processing. The actions service 609 may also handle prioritization and orchestration of multiple action threads. The response service 611 converts the text response into speech for presenting to the member if the user input is speech. The gateway service 601 sends the converted response back to the member through the portal 615 or IVR 617.

Figure 7:
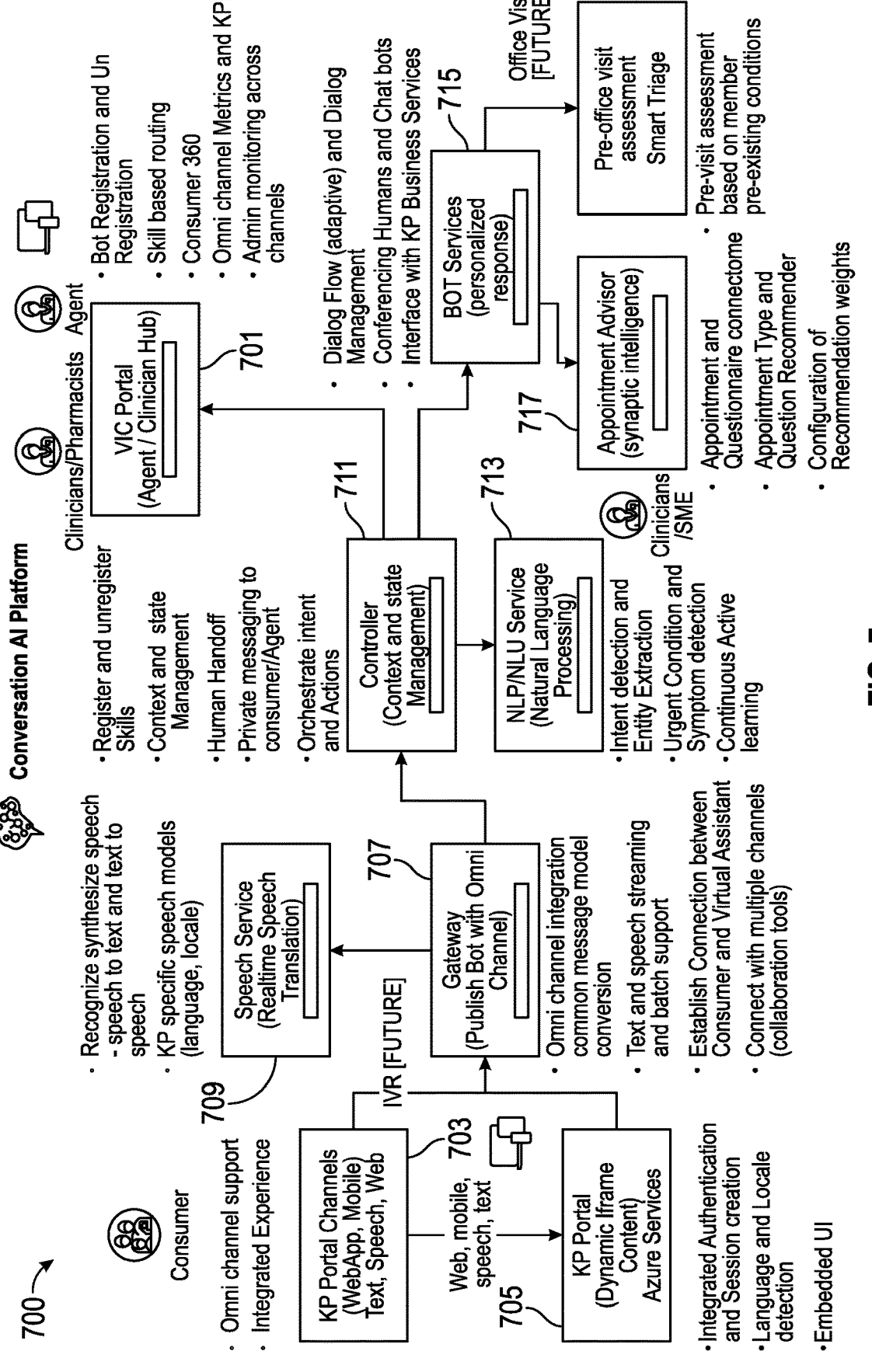
FIG. 7 is a block diagram illustrating another example implementation of an intelligent omnichannel conversational interface.

FIG. 7 is a block diagram 700 illustrating another example implementation of an intelligent omnichannel conversational interface. For example, the intelligent omnichannel conversational interface may include an agent/clinician hub 701 may be used by clinicians or pharmacists as well as call center agents. Telehealth interface 335 and call routing management 340, as shown in FIG. 3, may be performed through the agent/clinician hub 701. The agent/clinician hub 701 may also be used for specialized bot registration and un-registration. For example, specialized bots 330, as described above with respect to FIG. 3, may be registered based on new diseases or other operational needs. Similarly, specialized bots may be unregistered when the need has passed. Skill based routing, consumer 360, omni channel metrics and KPI, and admin monitoring across channels may be included in the agent/clinician hub 701. Dynamic Iframe Content 705 may operate as a portal for integrated authentication and session creation, detect language and locale, and operate as an embedded user interface. Portal channels 703 may include a web application and mobile application to provide omni channel support to consumers and an integrated experience over text, speech, and web. Portal channels 703 represent the digital interface 305, self-service interface 310, telephony interface 315, and interactive voice response 320 of the conversation interface application 110 depicted in FIG. 3.

Figure 8A:
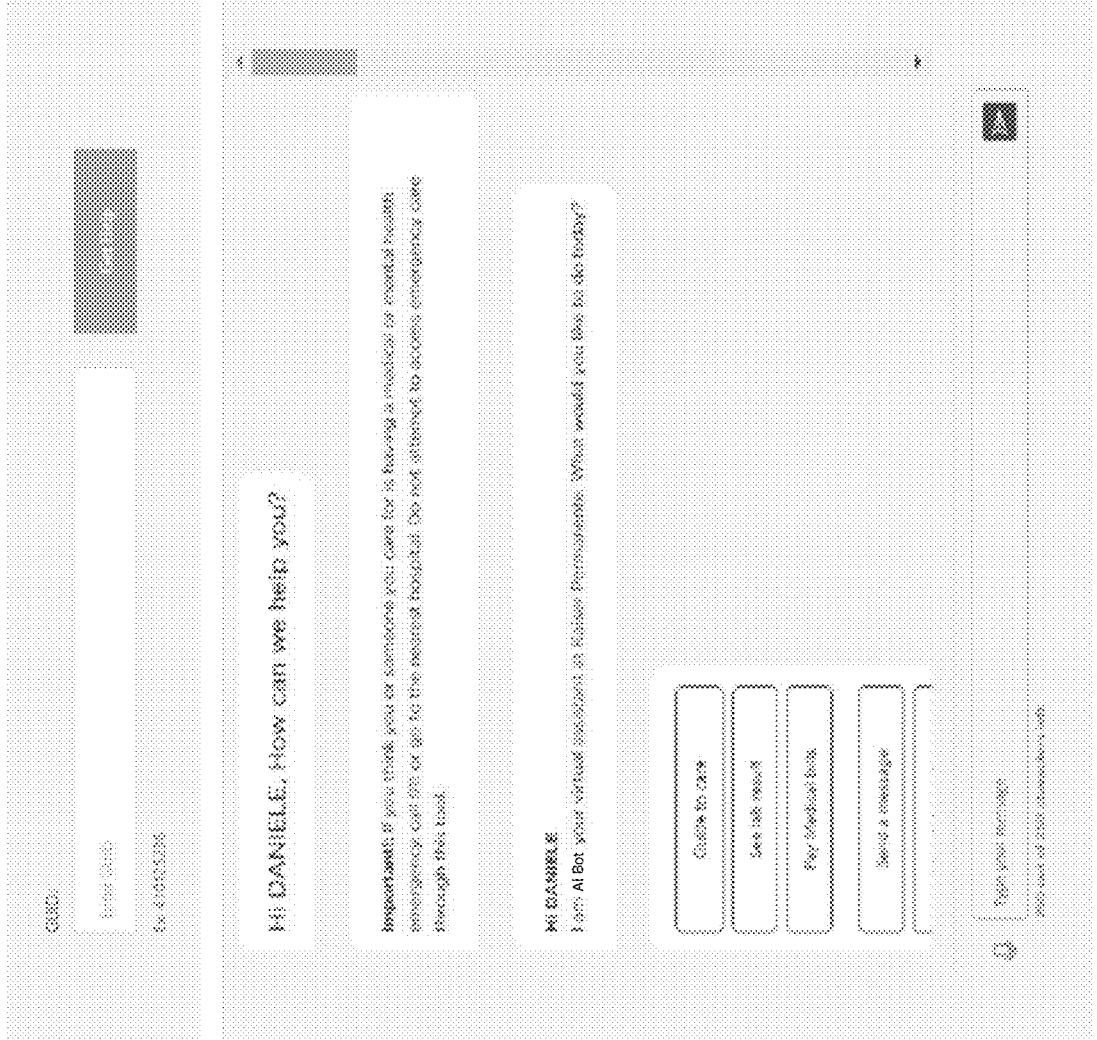
Figure 8A:
Figure 8D:
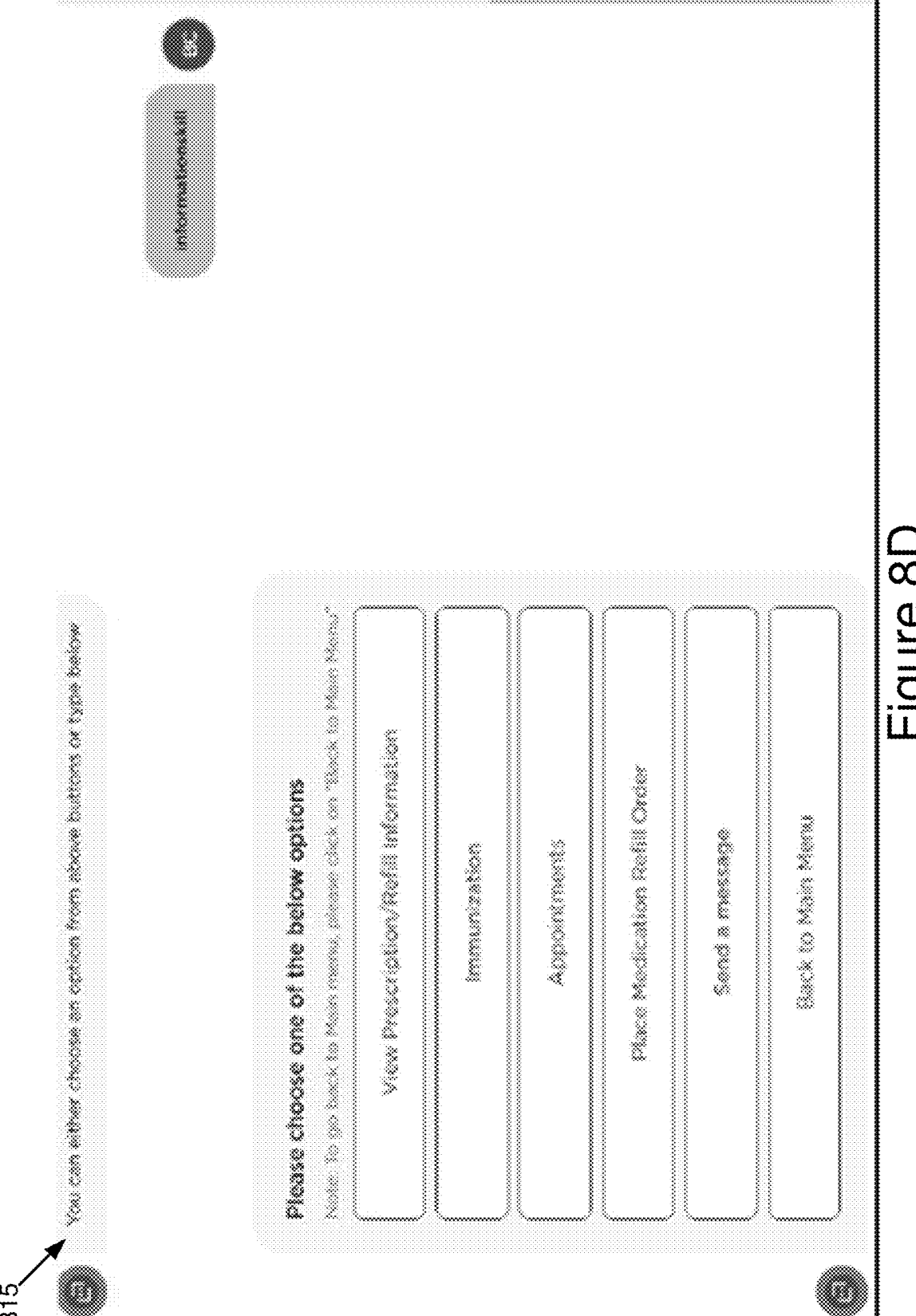
Figure 8E:
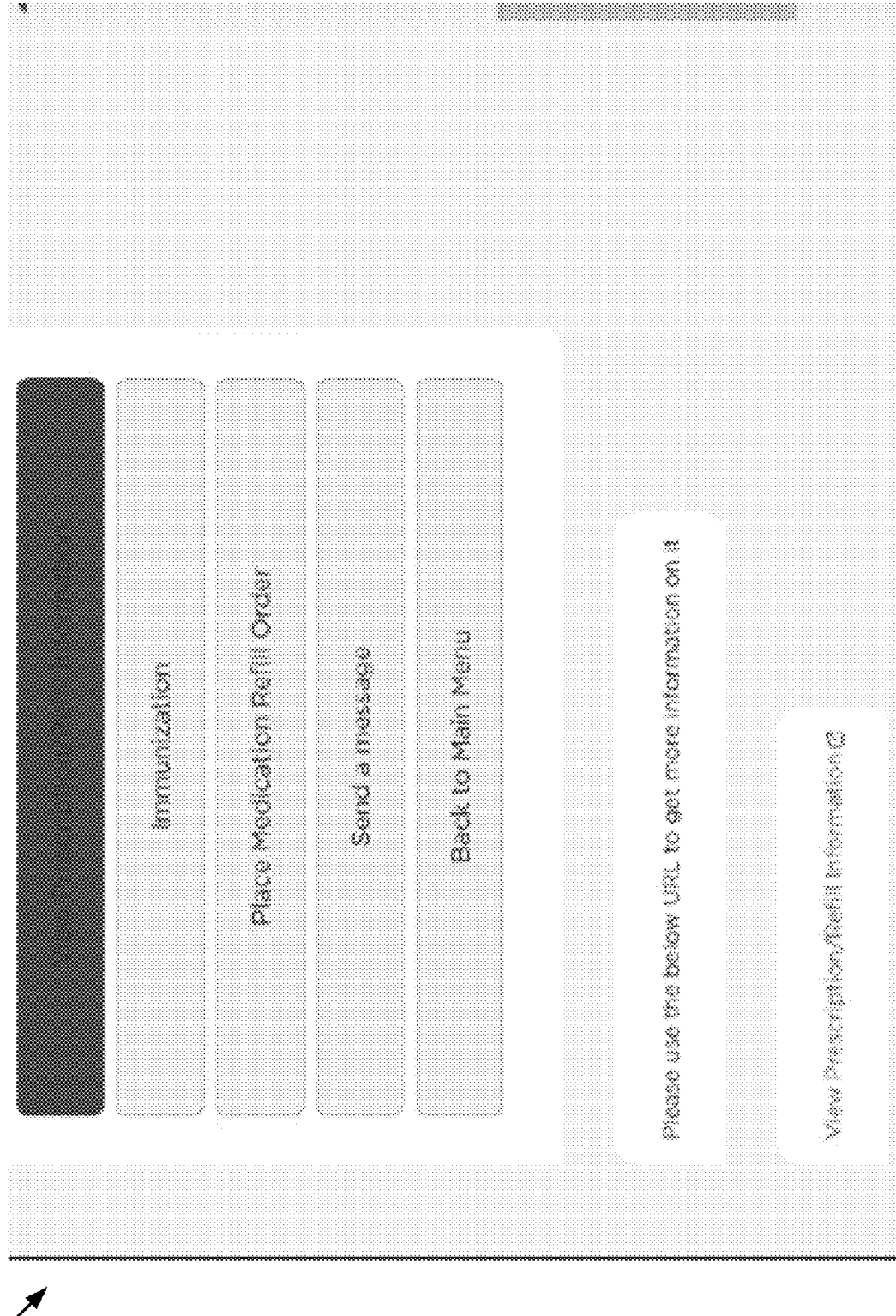
Figure 8F:
Figure 8F:
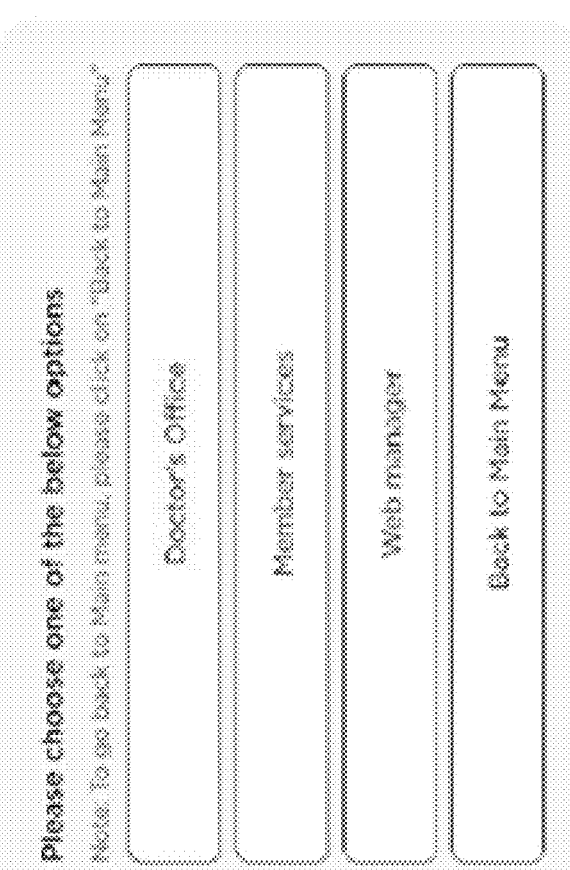
Figure 8G:
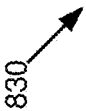
Figure 8G:
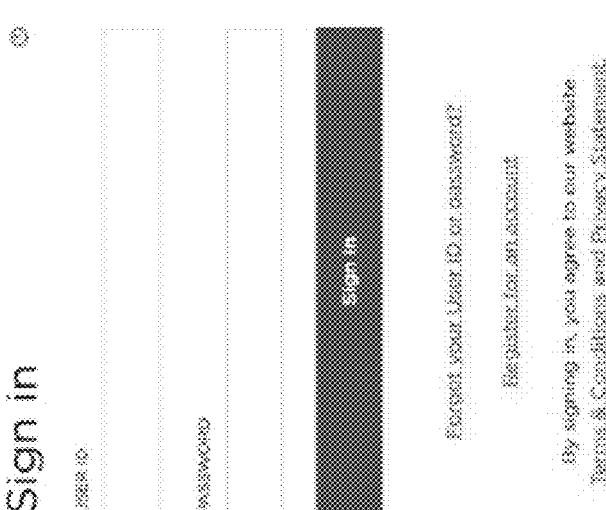
Figure 8G:

FIGS. 8A-8G are graphical representations of example user interfaces of a patient member accessing the conversational interface for answers to health-related queries. In FIG. 8A, the graphical representation 900 of a user interface includes a field for the patient member to enter their identifier number to get help and the conversational interface includes virtual assistant or bot to help the member with their requests. In FIG. 8B, the graphical representation 805 includes several options for the patient member to choose. If the member chooses "Guide to Care" option, the member is directed to a webpage shown in FIG. 8C. If the member chose either "See lab result," or "Pay Medical Bills," the member is directed to the login page shown in FIG. 8G to login in their account with the healthcare organization where they may see their lab results or pay medical bills. If the member chose "Your information," the virtual assistant or bot presents further options to select from as shown in FIG. 8D. In FIG. 8D, if the member selected either "View prescription/refill information," "Immunization," "Appointments," or "Place Medical Refill Order" the member is directed to the login page shown in FIG. 8G to login in their account with the healthcare organization to complete the actions. In FIG. 8D, if the member chose "Send a message," the virtual assistant or bot presents further options to select from as shown in FIG. 8F. In FIG. 8F, if the member chose any one of the options, the virtual assistant or bot directs them to the login page shown in FIG. 8G to login in their account with the healthcare organization to complete the actions.

Figure 9A:
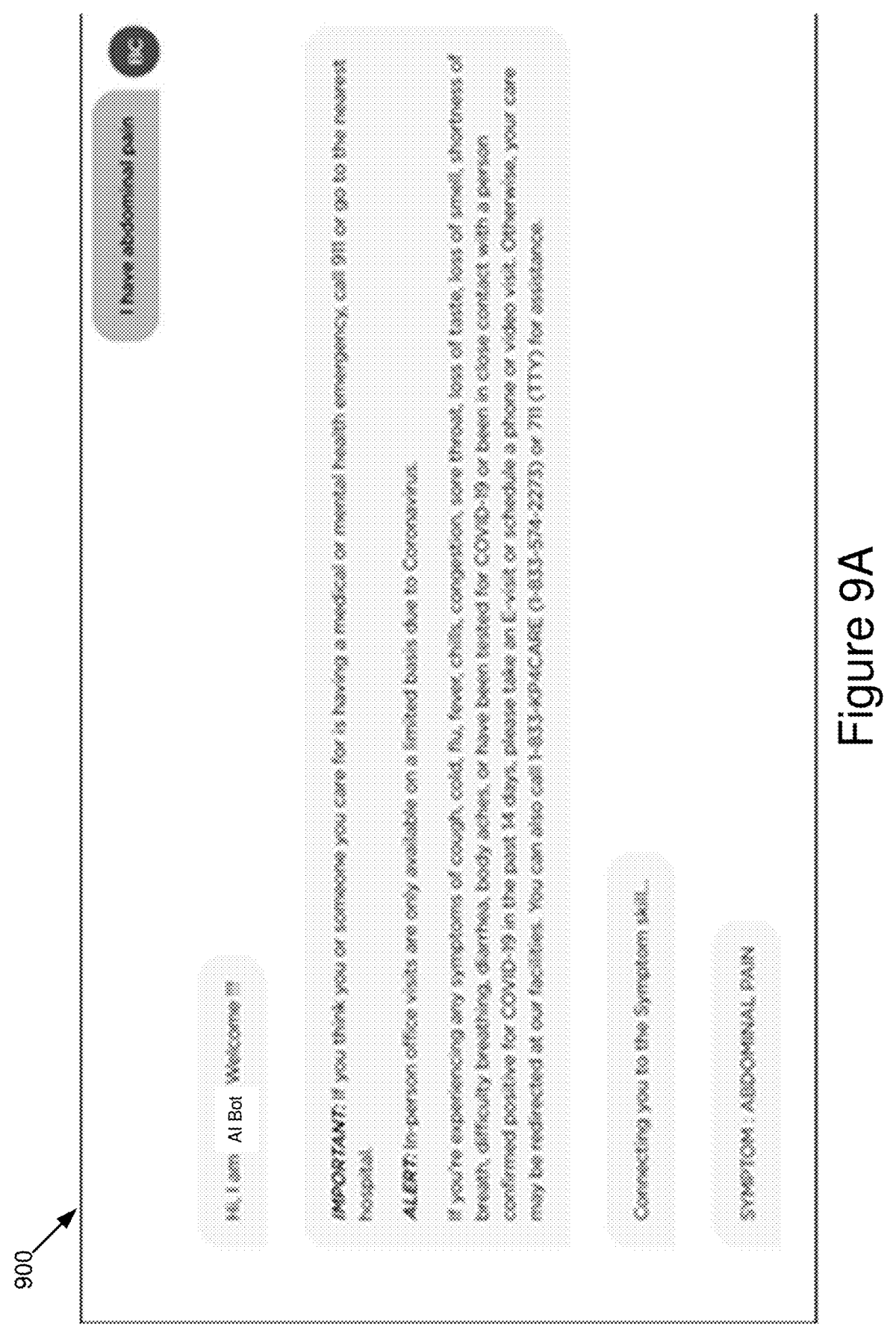
Figure 9B:
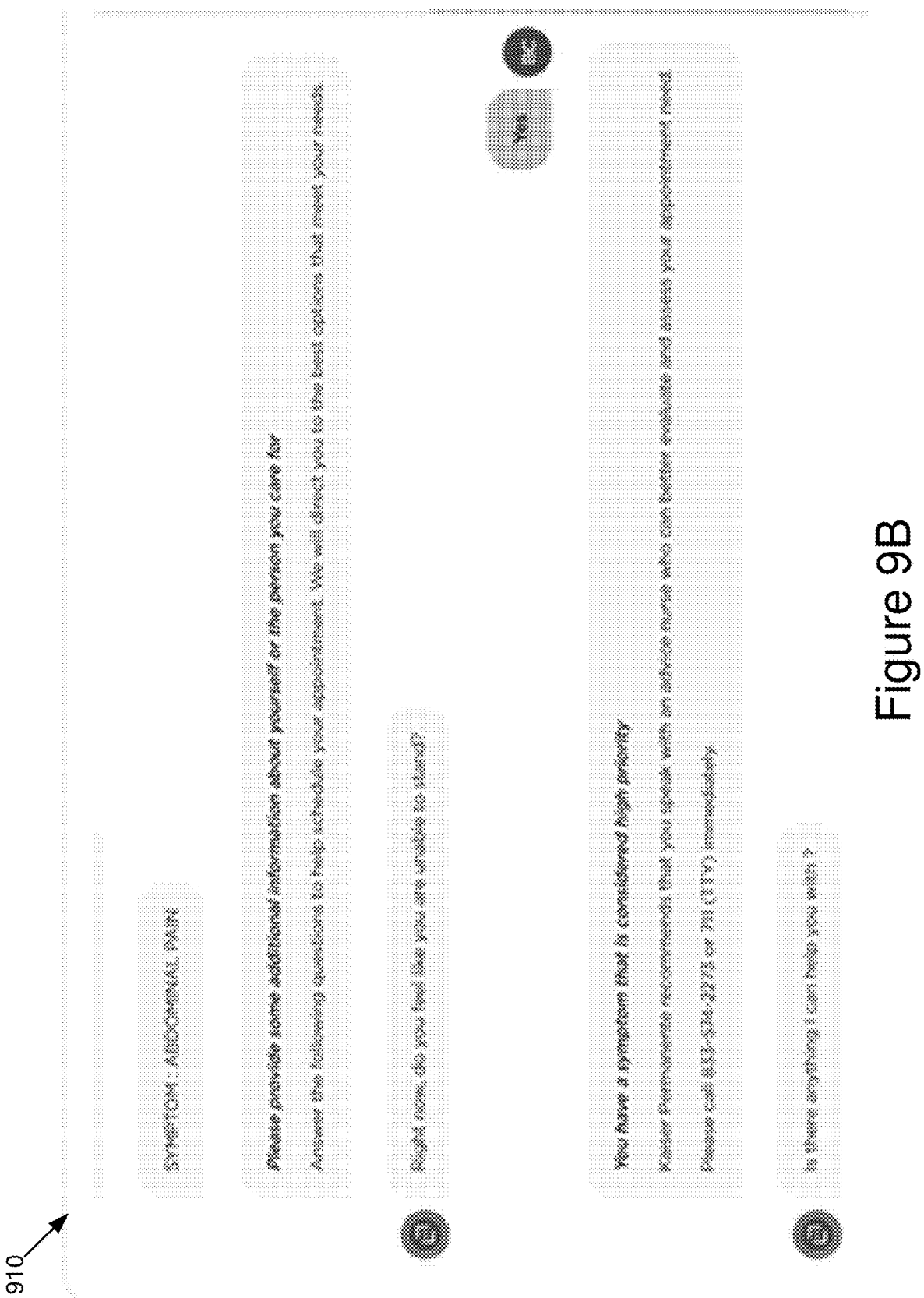

FIGS. 9A-9K are graphical representations of example user interfaces of a patient member accessing the conversational interface in an appointment booking workflow. In FIG. 9A, the graphical representation 900 of a user interface includes a virtual healthcare chatbot welcoming a patient member. When the patient member enters "I have abdominal pain" into the message window, the conversational interface application 110 identifies the symptom or reason for appointment as "Abdominal Pain." In FIG. 9B, the graphical representation 910 of the user interface displays a series of questions for the patient member to answer further. Based on the answers, the conversational interface application 110 determines whether the symptom indicates a high priority health condition. If it is, the graphical representation 910 of the user interface recommends the patient member to speak with an advice nurse immediately.

Figure 9C:
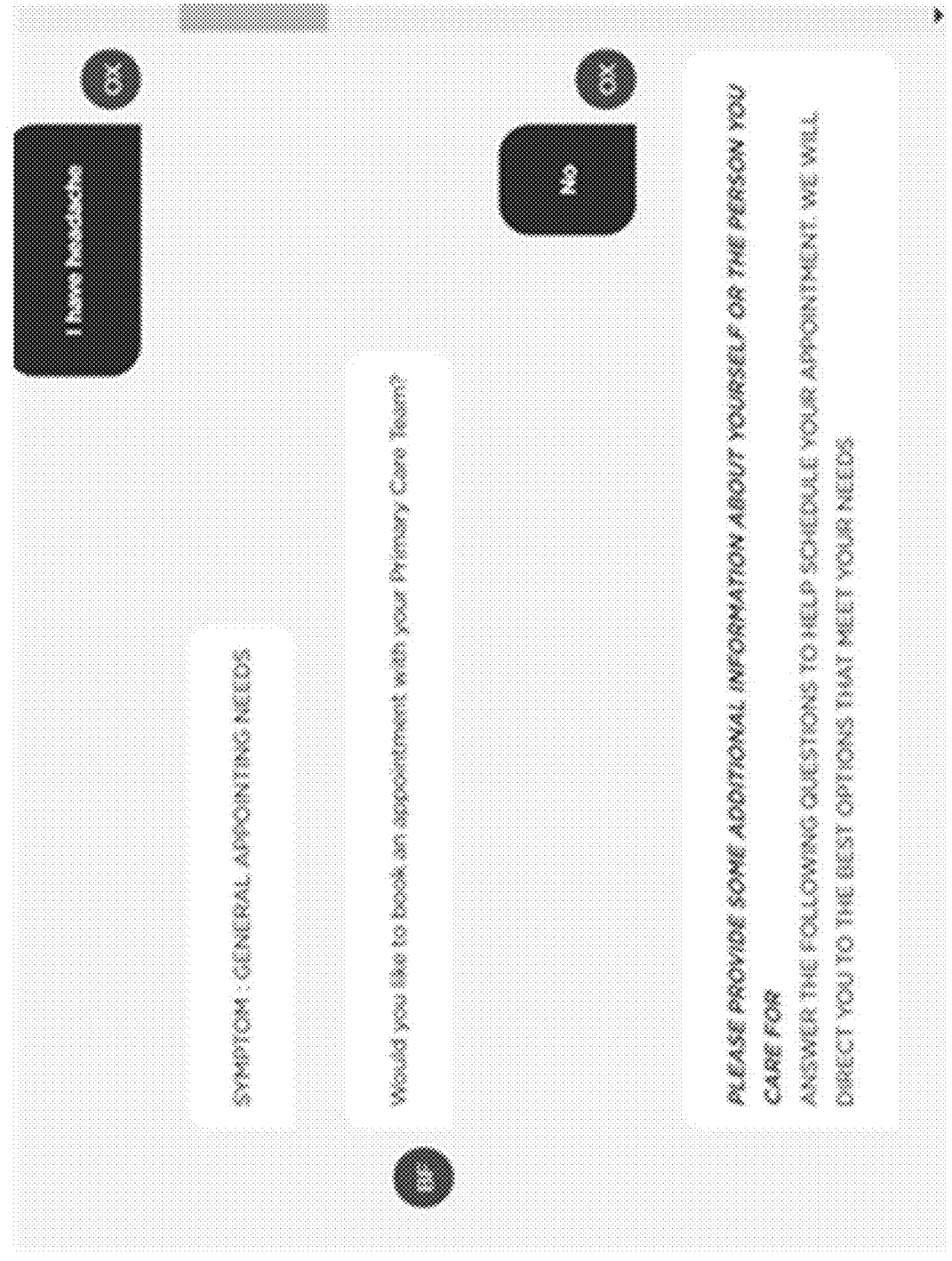
Figure 9D:
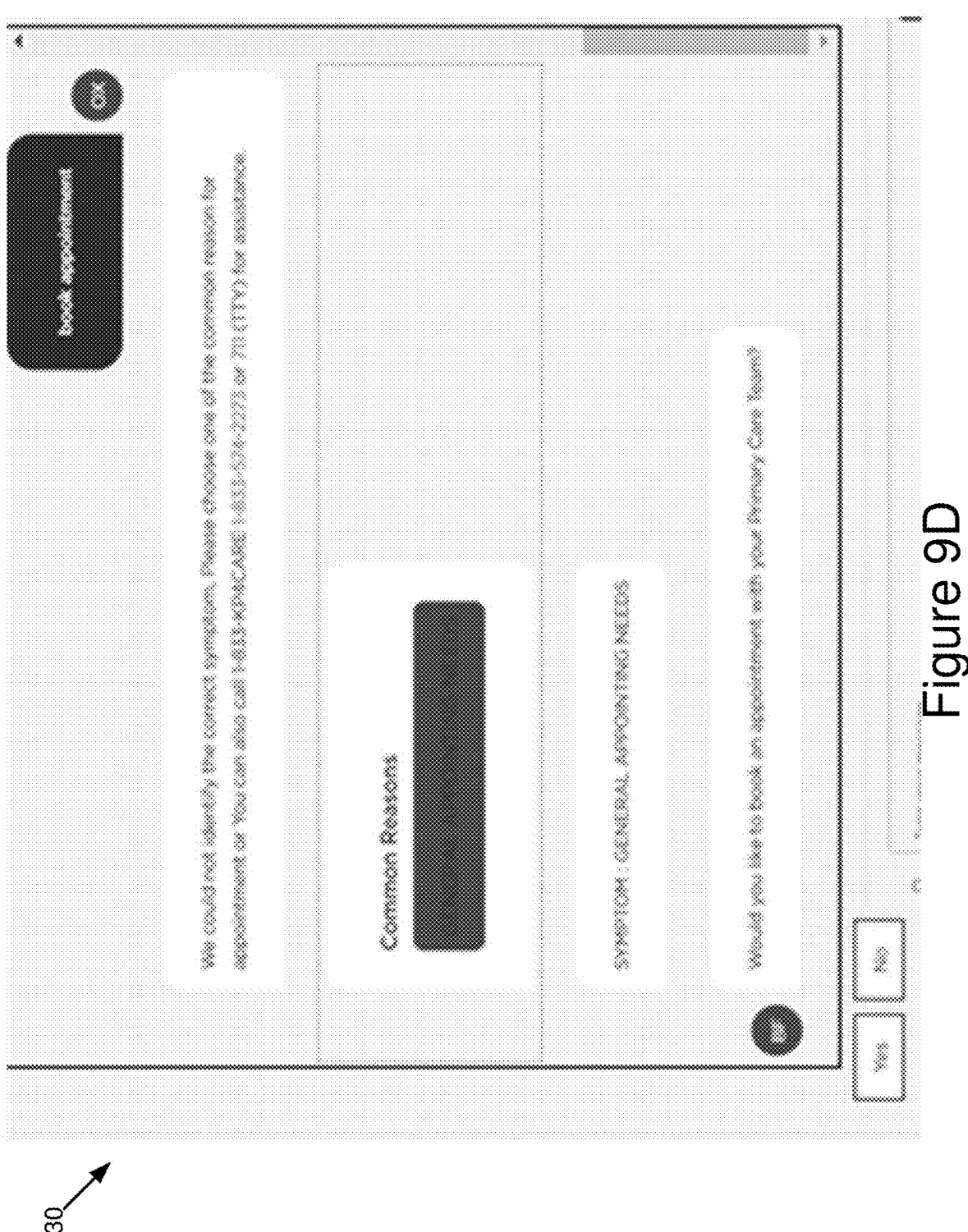
Figure 9E:
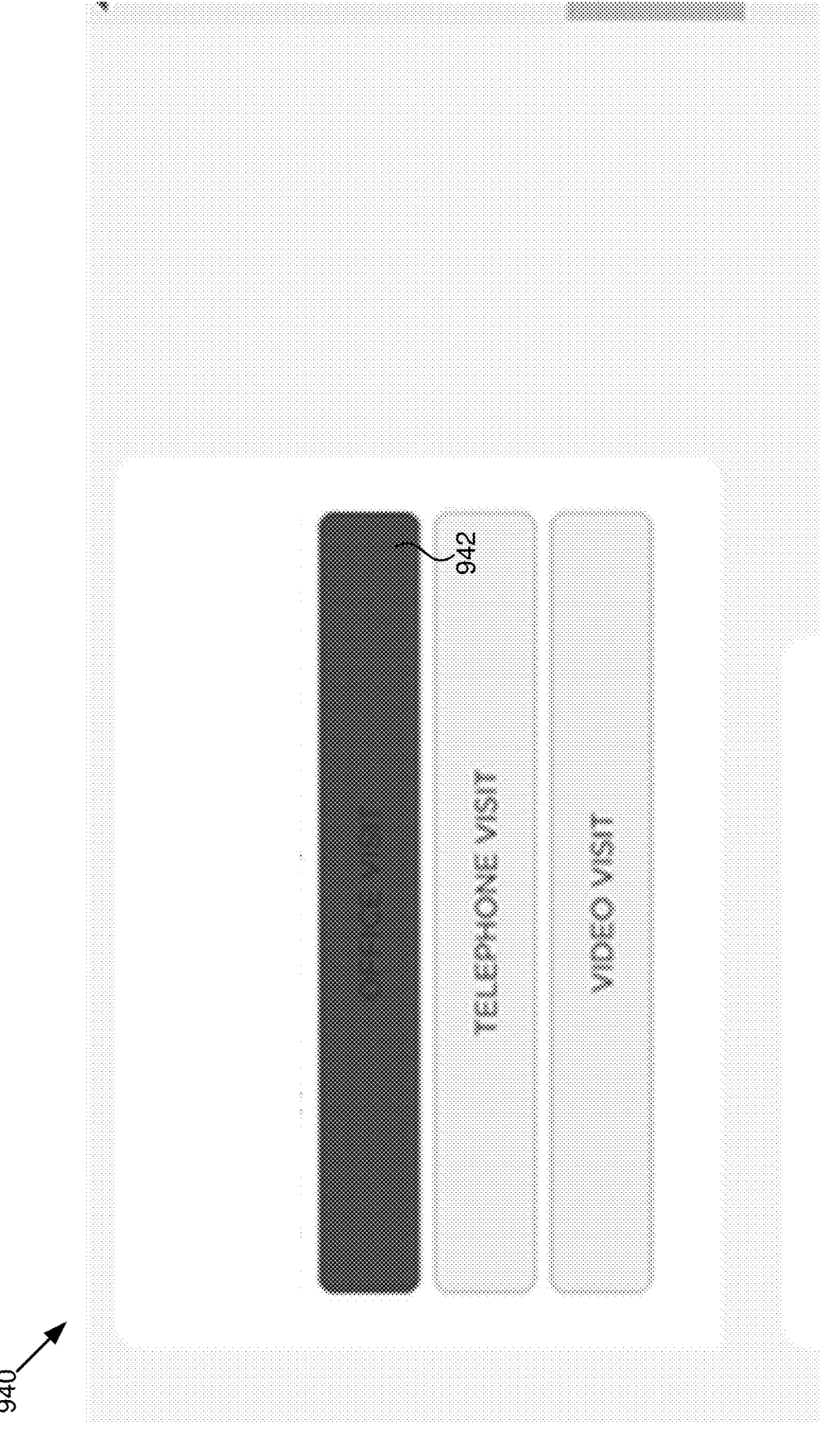
Figure 9F:
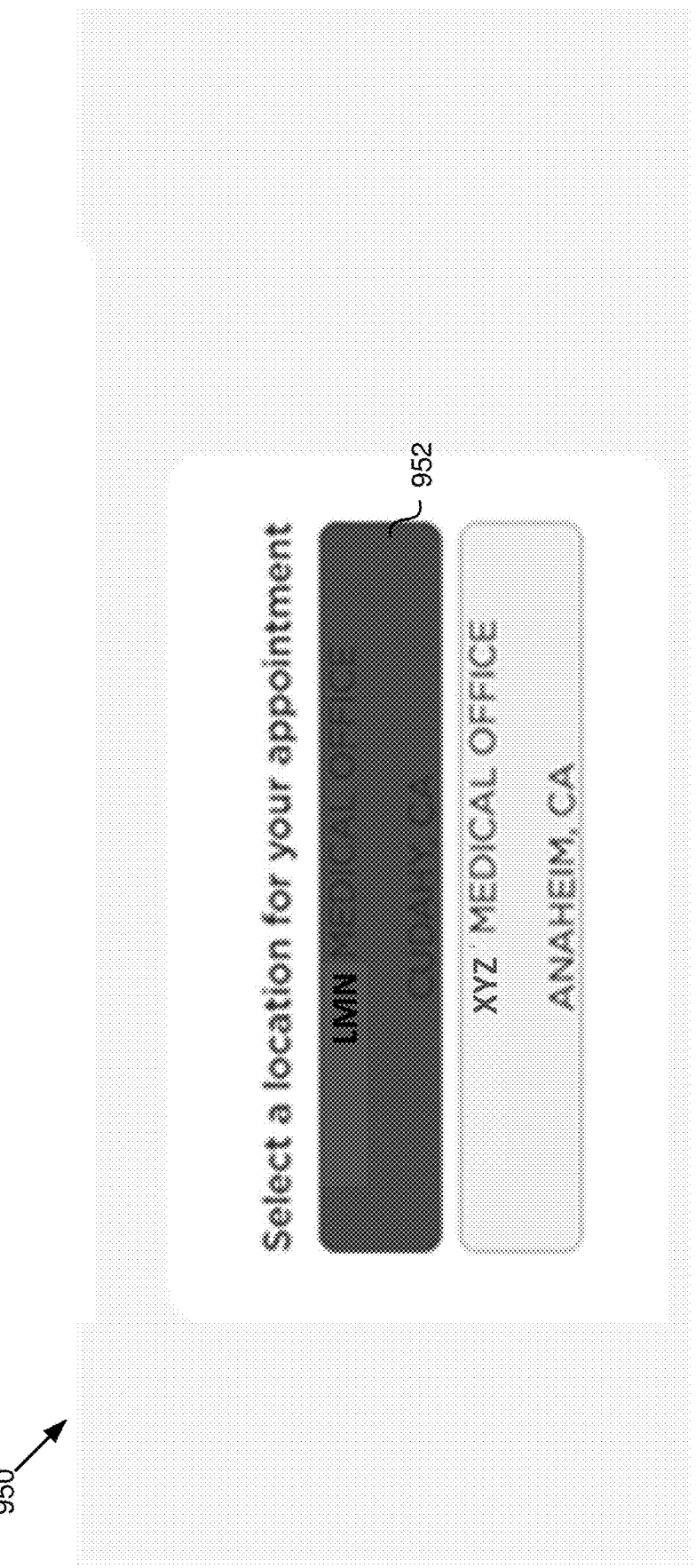
Figure 9G:
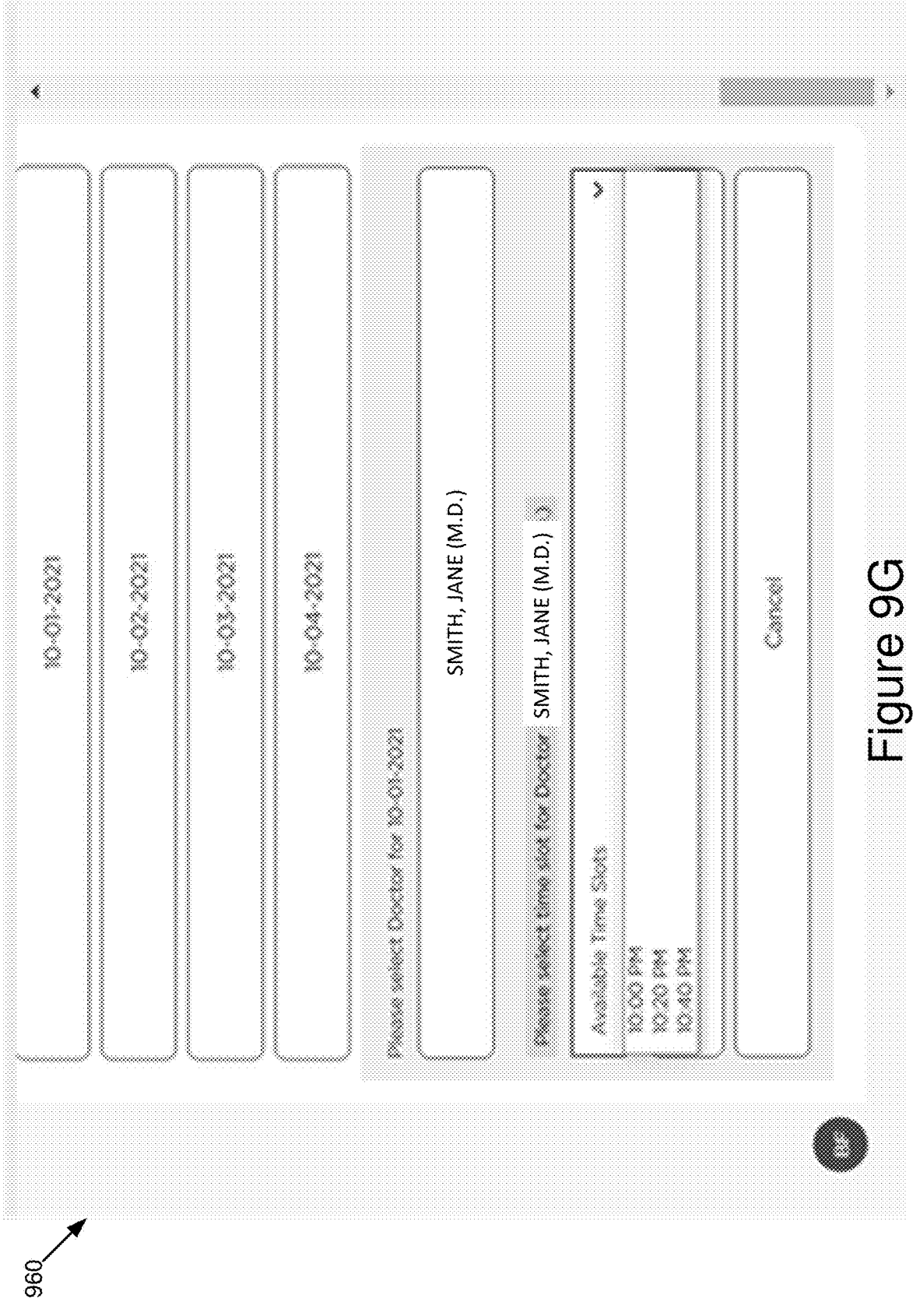
Figure 9H:
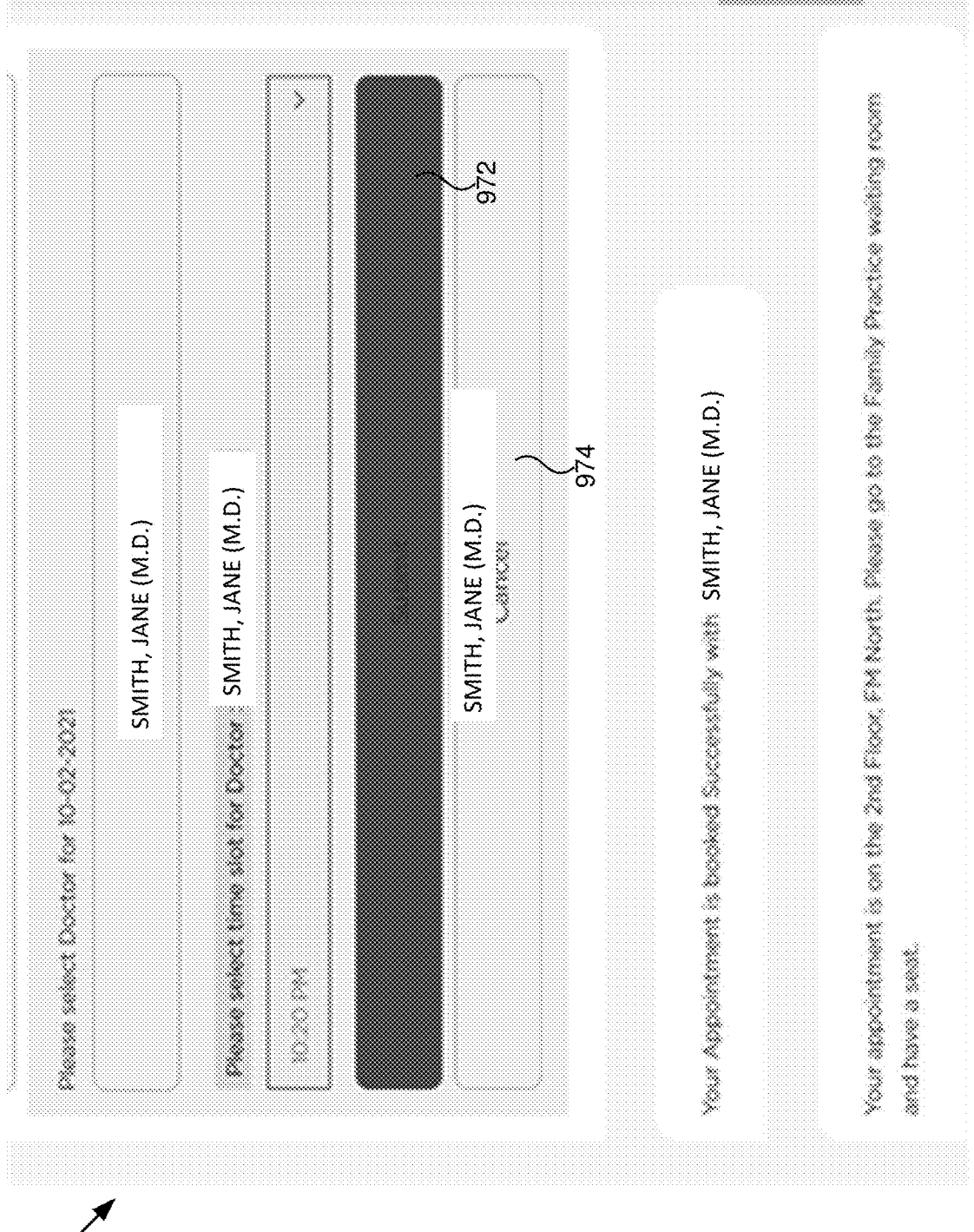
Figure 9I:
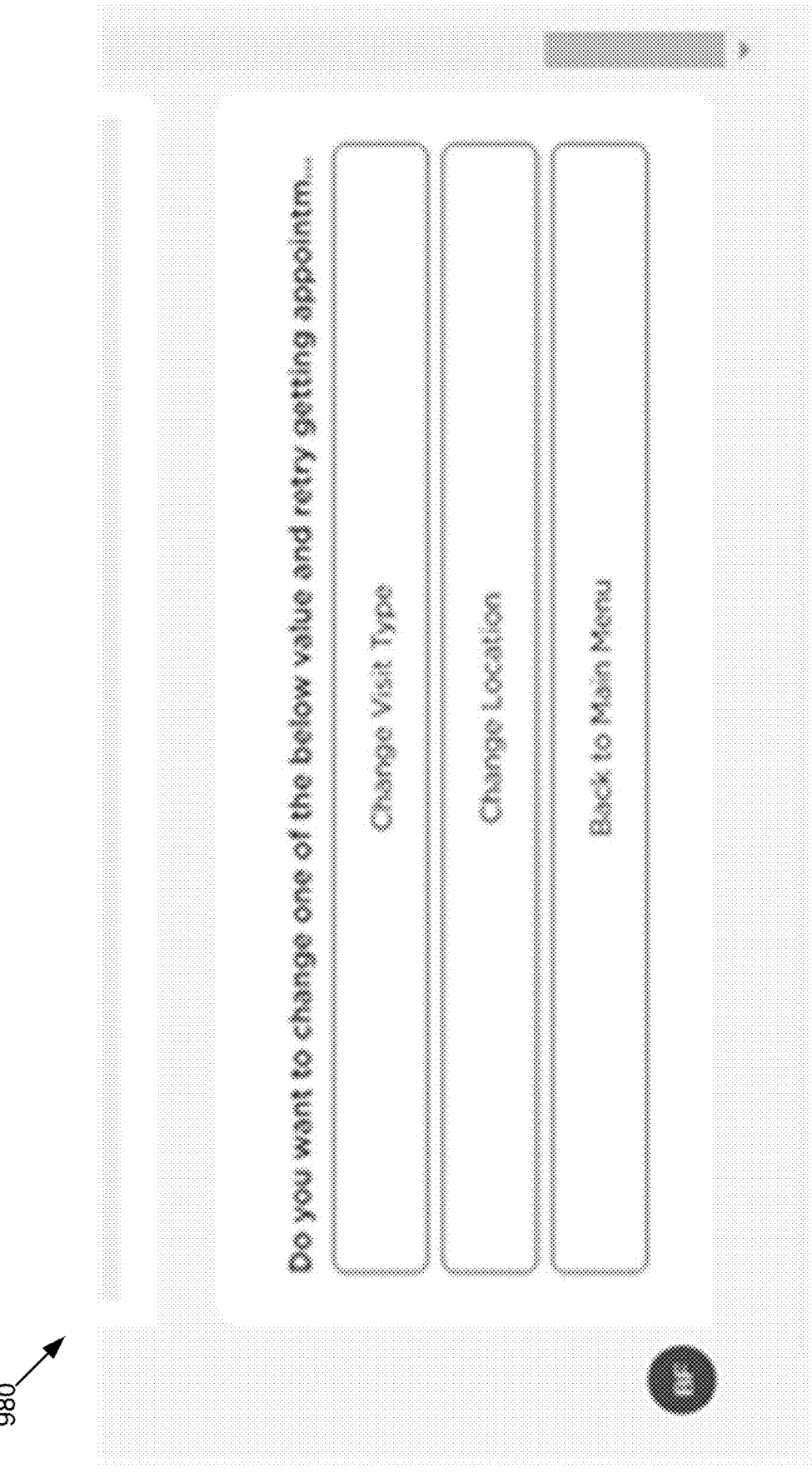
Figure 9J:
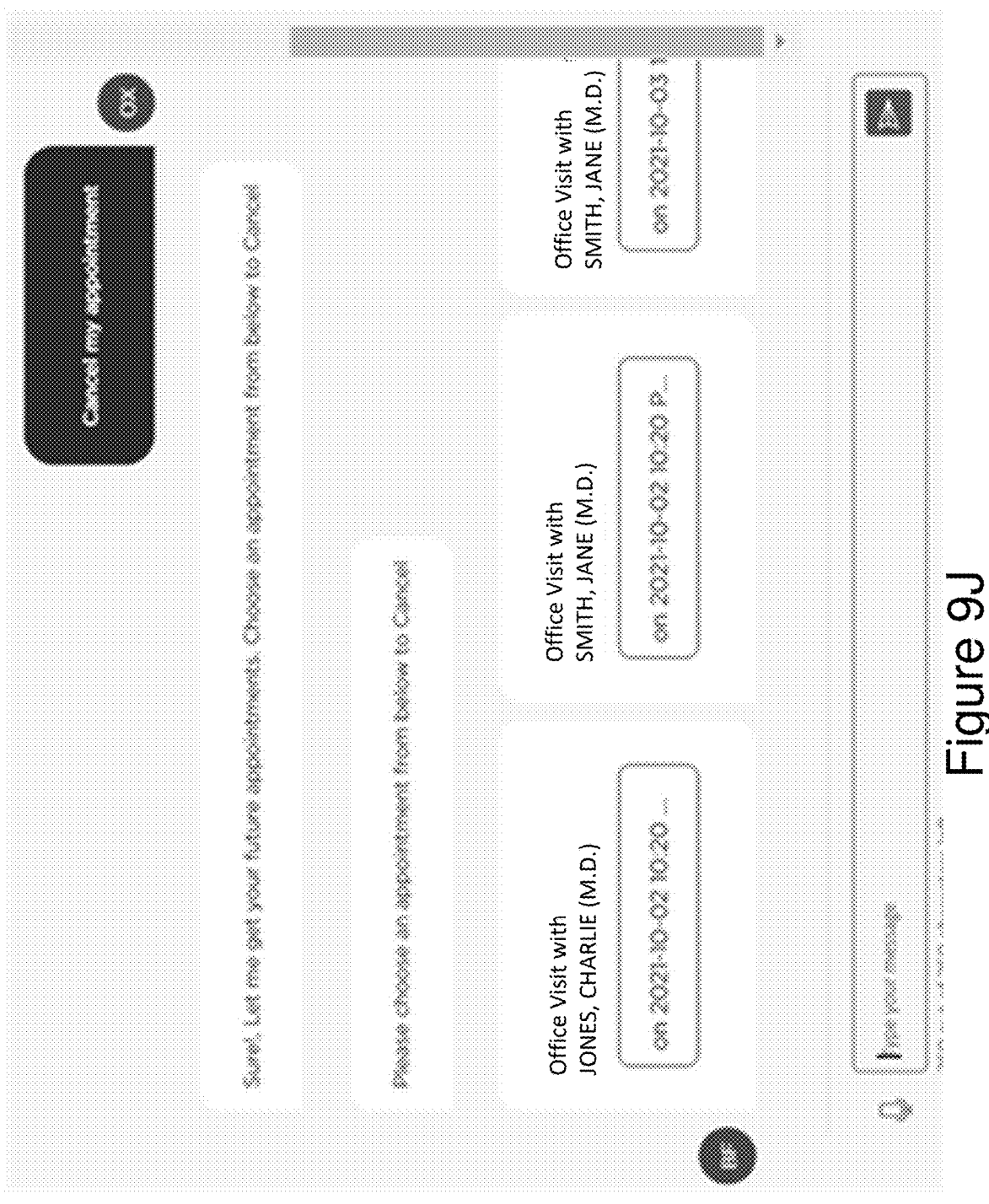
Figure 9K:
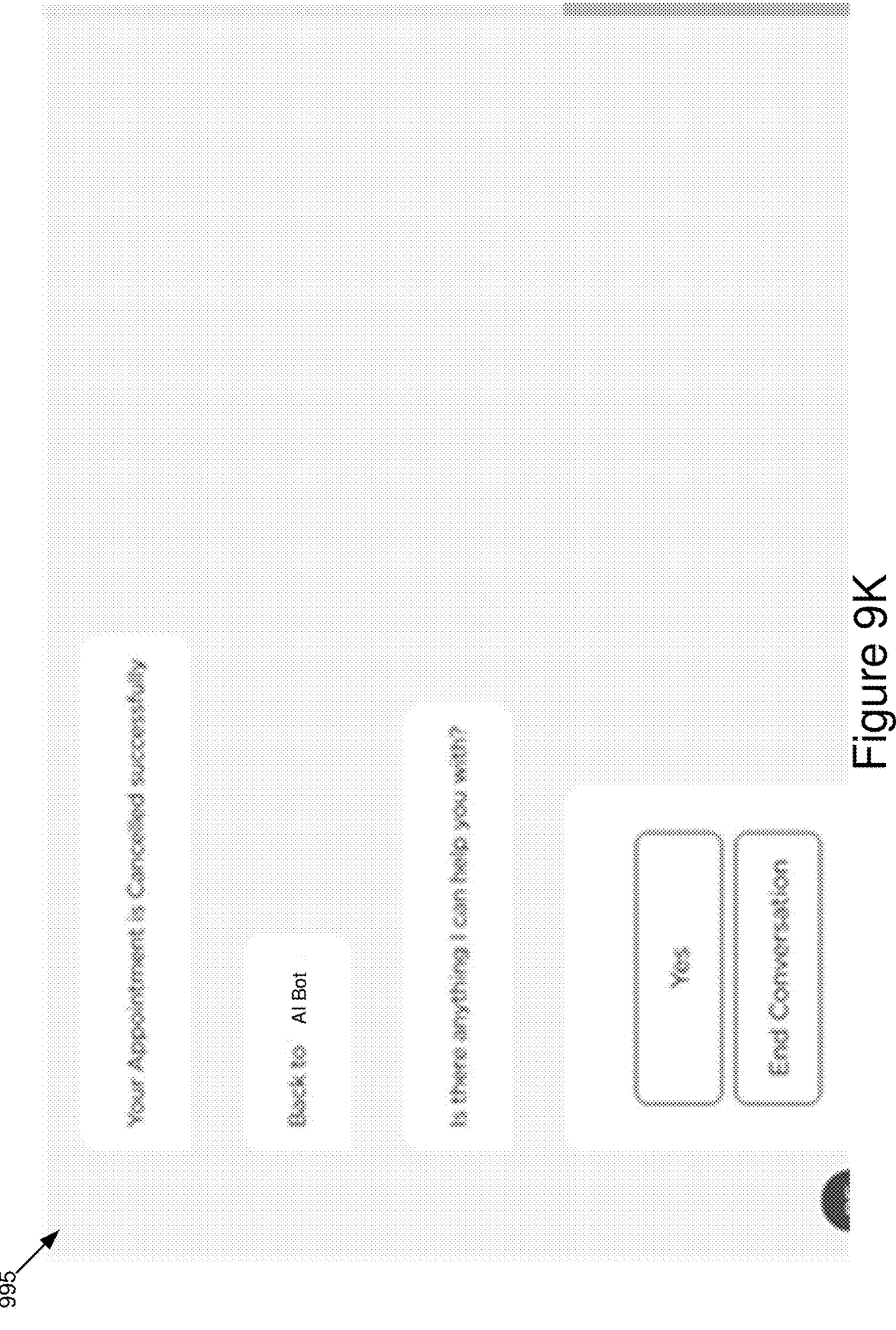

In FIG. 9C, the graphical representation 920 of the user interface displays the message window where the patient member has entered "I have headache." The conversational interface application 110 determines the symptom does not indicate a high priority health condition and directs the user to connect with a primary care physician. Alternatively, in FIG. 9D, the graphical representation 930 of the user interface displays the message window where the patient member has entered "book appointment." The conversational interface application 110 determines that the reason for appointment is general appointment needs and directs the user to connect with the primary care physician. In FIG. 9E, the conversational interface application 110 recommends the appointment modalities suited for the patient member in a ranking order. For example, the patient member who is 65 years old prefers office visits for appointments. The conversational interface application 110 visually distinguishes the office visit modality from the other appointment modalities for the patient member. The patient member may select the recommendation of the office visit 942. In FIG. 9F, the graphical representation 950 of the user interface lists the locations for the office visit modality selected by the patient member. The locations may also be recommendations for the patient member based on their geoscore. The patient member may select the recommendation of the location 952. In FIG. 9G, the graphical representation 960 of the user interface displays available appointment dates, slots, and doctor for providing care to the patient member. In FIG. 9H, when the patient member selects submit button 972 in the graphical representation 970 of the user interface, the conversational interface application 110 books the appointment for the patient member. If the patient member selects cancel button 974, the conversational interface application 110 directs the patient member to FIG. 9I. In FIG. 9I, the graphical representation 980 of the user interface allows the patient member to change the visit type and the location for their appointment. In FIG. 9J, the graphical representation 990 of the user interface displays a message window where the patient member may request the virtual chatbot to cancel a booked appointment. For example, the patient member may enter text "Cancel my appointment" and the conversational interface application 110 retrieves and displays all booked appointments of the patient member. The patient member may select one or more booked appointments to cancel. In FIG. 9K, the graphical representation 995 of the user interface displays a confirmation that a booked appointment selected by the patient member in FIG. 9J is canceled successfully.

The user interface engine 208 may include software and/or logic for providing user interfaces to a user. In some implementations, the user interface engine 208 receives instructions from the components 202, 204, and 206, generates a user interface according to the instructions, and transmits the user interface for display on the client device 115. In some implementations, the user interface engine 208 sends graphical user interface data to an application (e.g., a browser) in the client device 115 via the communication unit 241 causing the application to display the data as a graphical user interface.

FIG. 10 is an example flowchart diagram of a method 1000 of accessing the conversational interface for health-related queries. Method 1000 may begin with user input being received 1002 from a patient member user through an interactive conversational interface. For example, a patient member user may operate a mobile application to enter text, such as "I have abdominal pain." As another example, the mobile application may enable omnichannel support, such as telephony interface to call a call center agent, a self-service interface to enable the patient member user to complete actions, such as booking an appointment for an in-office visit, meeting with a nurse practitioner for a video visit more urgently, or receiving information related to the user input. Additionally, different channels of communication can be utilized and orchestrated, enabling different types of user input to be received from the different channels. For example, in a situation where the patient member user enters user input regarding a need to refill a prescription and a request to talk to a nurse about a rash, the two items may be prioritized and orchestrated separately.

One or more health conditions associated with the patient member user is determined 1004 based on the received user input. Using one or more natural language processing (NLP) models, the one or more health conditions may be determined 1004. In this way, the conversational interface understands the intent of the user to seek access to health care for the determined one or more health conditions. The determined one or more health conditions and a series of questions related to the one or more health conditions are presented 1006 to the patient member user. For example, additional questions related to a determined health condition of "abdominal pain" may be retrieved from a data store of questions, such as "Right now, do you feel like you are unable to stand?" as illustrated in FIG. 9B. Responses to the series of questions are then received 1008. One or more recommended actions for the patient member user to access health care related to the one or more health conditions are determined 1010 based on the received responses using one or more machine learning models. For example, the response to the question regarding abdominal pain of "Yes" may be linked to a high priority or high acuity symptom associated with the health condition of "abdominal pain." The recommended action, as illustrated in FIG. 9B, is to call an advice nurse immediately.

Based on one or more actions performed by the patient member user, one or more additional recommended actions may be generated 1012, optionally. For example, the patient member user may enter other user input or request a video visit. Other recommended actions may be generated, such as providing wellness information related to the determined symptom and/or routing the user to a video urgent visit. Lastly, the one or more machine learning models used to generate the one or more recommended actions and the one or more additional recommended actions may be trained 1014 based on one or more actions performed by the patient member user. For example, the one or more machine learning models may be periodically trained based on the responses of the patient member user as well as other users of the conversational interface.

A system and method for providing patients with access to care for appropriate healthcare services using an intelligent omnichannel conversational interface has been described. In the above description, for purposes of explanation, numerous specific details are set forth in order to provide a thorough understanding of the techniques introduced above. It will be apparent, however, to one skilled in the art that the techniques can be practiced without these specific details. In other instances, structures and devices are shown in block diagram form in order to avoid obscuring the description and for ease of understanding. For example, the techniques are described in one implementation above primarily with reference to software and particular hardware. However, the present invention applies to any type of computing system that can receive data and commands, and present information as part of any peripheral devices providing services.

Reference in the specification to "one implementation" or "an implementation" means that a particular feature, structure, or characteristic described in connection with the implementation is included in at least one implementation. The appearances of the phrase "in one implementation" in various places in the specification are not necessarily all referring to the same implementation.

Some portions of the detailed descriptions described above are presented in terms of algorithms and symbolic representations of operations on data bits within a computer memory. These algorithmic descriptions and representations are, in some circumstances, used by those skilled in the data processing arts to convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing", "computing", "calculating", "determining", "displaying", or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The techniques also relate to an apparatus for performing the operations herein. This apparatus may be specially constructed for the required purposes, or it may comprise a general-purpose computer selectively activated or reconfigured by a computer program stored in the computer. Such a computer program may be stored in a non-transitory computer readable storage medium, such as, but is not limited to, any type of disk including floppy disks, optical disks, CD-ROMs, and magnetic disks, read-only memories (ROMs), random access memories (RAMs), EPROMs, EEPROMs, magnetic or optical cards, flash memories including USB keys with non-volatile memory or any type of media suitable for storing electronic instructions, each coupled to a computer system bus.

The technology described herein can take the form of a hardware implementation, a software implementation, or implementations containing both hardware and software elements. For instance, the technology may be implemented in software, which includes but is not limited to firmware, resident software, microcode, etc. Furthermore, the technology can take the form of a computer program product accessible from a computer-usable or computer-readable medium providing program code for use by or in connection with a computer or any instruction execution system. For the purposes of this description, a computer-usable or computer readable medium can be any non-transitory storage apparatus that can contain, store, communicate, propagate, or transport the program for use by or in connection with the instruction execution system, apparatus, or device.

A data processing system suitable for storing and/or executing program code may include at least one processor coupled directly or indirectly to memory elements through a system bus. The memory elements can include local memory employed during actual execution of the program code, bulk storage, and cache memories that provide temporary storage of at least some program code in order to reduce the number of times code must be retrieved from bulk storage during execution. Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems, storage devices, remote printers, etc., through intervening private and/or public networks. Wireless (e.g., Wi-Fi™) transceivers, Ethernet adapters, and modems, are just a few examples of network adapters. The private and public networks may have any number of configurations and/or topologies. Data may be transmitted between these devices via the networks using a variety of different communication protocols including, for example, various Internet layer, transport layer, or application layer protocols. For example, data may be transmitted via the networks using transmission control protocol/Internet protocol (TCP/IP), user datagram protocol (UDP), transmission control protocol (TCP), hypertext transfer protocol (HTTP), secure hypertext transfer protocol (HTTPS), dynamic adaptive streaming over HTTP (DASH), real-time streaming protocol (RTSP), real-time transport protocol (RTP) and the real-time transport control protocol (RTCP), voice over Internet protocol (VOIP), file transfer protocol (FTP), Web-Socket (WS), wireless access protocol (WAP), various messaging protocols (SMS, MMS, XMS, IMAP, SMTP, POP, WebDAV, etc.), or other known protocols.

Finally, the structure, algorithms, and/or interfaces presented herein are not inherently related to any particular computer or other apparatus. Various general-purpose systems may be used with programs in accordance with the teachings herein, or it may prove convenient to construct more specialized apparatus to perform the required method blocks. The required structure for a variety of these systems will appear from the description above. In addition, the specification is not described with reference to any particular programming language. It will be appreciated that a variety of programming languages may be used to implement the teachings of the specification as described herein.

The foregoing description has been presented for the purposes of illustration and description. It is not intended to be exhaustive or to limit the specification to the precise form disclosed. Many modifications and variations are possible in light of the above teaching. It is intended that the scope of the disclosure be limited not by this detailed description, but by the claims of this application. As will be understood by those familiar with the art, the specification may be embodied in other specific forms without departing from the spirit or essential characteristics thereof. Likewise, the particular naming and division of the modules, routines, features, attributes, methodologies, and other aspects are not mandatory or significant, and the mechanisms that implement the specification or its features may have different names, divisions and/or formats.

Furthermore, the modules, routines, features, attributes, methodologies, engines, and other aspects of the disclosure can be implemented as software, hardware, firmware, or any combination of the foregoing. Also, wherever an element, an example of which is a module, of the specification is implemented as software, the element can be implemented as a standalone program, as part of a larger program, as a plurality of separate programs, as a statically or dynamically linked library, as a kernel loadable module, as a device driver, and/or in every and any other way known now or in the future. Additionally, the disclosure is in no way limited to implementation in any specific programming language, or for any specific operating system or environment. Accordingly, the disclosure is intended to be illustrative, but not limiting, of the scope of the subject matter set forth in the following claims.

What is claimed is:

1. A method comprising:

receiving multiple different requests regarding a patient member user, a first request of the multiple different requests including user input received through a conversational interface application and a second request of the multiple different requests received from an engagement channel different from the conversational interface application;

generating, using a user interaction engine, a user interaction history comprising a consolidated data stream including the multiple different requests, wherein the user interaction engine generates the consolidated data stream accessible by the conversational interface application through a conversational interface engine that receives a batch of conversational text including the second request of the multiple different requests received from the engagement channel;

determining an applicable intent of the patient member user based on the user interaction history, the applicable intent of the patient member user determined by a first machine learning model created to identify the applicable intent from the multiple different requests;

retrieving, from data storage, a screening questionnaire comprising one or more questions associated with the applicable intent of the patient member user, the screening questionnaire retrieved using one or more specialized bots generated to handle a specific health condition, the screening questionnaire associated with the specific health condition;

presenting the one or more questions to the patient member user through the conversational interface application;

receiving one or more responses to the one or more questions through the conversation interface application;

receiving training data on one or more mispronunciations of a spoken word utterance associated with the specific health condition, the training data on the one or more mispronunciations of the spoken word utterance received through a secure portal provided by a model training engine;

retraining, by the model training engine, the first machine learning model using the training data on the one or more mispronunciations of the spoken word utterance associated with the specific health condition;

retrieving data related to the patient member user, the data including the user input received through the conversational interface application and historical data regarding the specific health condition;

determining a second applicable intent of the patient member user based on the user interaction history, the second applicable intent of the patient member user determined by the first machine learning model retrained to identify the second applicable intent from the one or more mispronunciations of the spoken word utterance received through the secure portal provided by the model training engine;

determining one or more recommended actions to access a healthcare related to the specific health condition based on an output of a second machine learning model selected based on the second applicable intent, the historical data, and the data related to the patient member user, wherein the one or more responses and the user interaction history are used as input to the second machine learning model; and presenting the one or more recommended actions to the patient member user through the conversational interface application.

2. The method of claim 1, the method further comprising:

retrieving data related to the patient member user, the data including clinical data about the patient member user; and determining a third machine learning model based on the clinical data and the data related to the patient member user;

wherein the determining the one or more recommended actions to access the healthcare is also based on an output of the third machine learning model.

3. The method of claim 1, wherein one or more machine learning models are used in determining the applicable intent of the patient member user based on the user input, wherein the one or more machine learning models comprises a trained natural language understanding (NLU) model that classifies user input utterance and one or more of patient member profile, past medical and clinical history, and demographic data.

4. The method of claim 3, wherein the one or more machine learning models comprises at least one of a neural network, support vector machine, a decision tree, a Bayesian network, a random decision forest, a k-nearest neighbor, a linear regression, a least squares, and a hidden Markov model.

5. The method of claim 1, wherein the one or more recommended actions comprises at least one of an in-person office visit, a home visit, a phone call, a video visit, an email, a text, or an instant messaging chat.

6. The method of claim 1, wherein the conversational interface application includes at least one of a digital interface, a self-service interface, a telephony interface, or an interactive voice response (IVR).

7. The method of claim 1 further comprising:

receiving feedback from the patient member user completing the one or more recommended actions; and training one or more machine learning models based on the feedback.

8. A system comprising one or more processors and memory operably coupled with the one or more processors, wherein the memory stores instructions that, in response to execution of the instructions by the one or more processors, cause the one or more processors to perform operations including:

receiving multiple different requests regarding a patient member user, a first request of the multiple different requests including user input received through a conversational interface application and a second request of the multiple different requests received from an engagement channel different from the conversational interface application;

generating, using a user interaction engine, a user interaction history comprising a consolidated data stream including the multiple different requests, wherein the user interaction engine generates the consolidated data stream accessible by the conversational interface application through a conversational interface engine that receives a batch of conversational text including the second request of the multiple different requests received from the engagement channel;

determining an applicable intent of the patient member user based on the user interaction history, the applicable intent of the patient member user determined by a first machine learning model created to identify the applicable intent from the multiple different requests;

retrieving, from data storage, a screening questionnaire comprising one or more questions associated with the applicable intent of the patient member user, the screening questionnaire retrieved using one or more specialized bots generated to handle a specific health condition, the screening questionnaire associated with the specific health condition;

presenting the one or more questions to the patient member user through the conversational interface application;

receiving one or more responses to the one or more questions through the conversation interface application;

receiving training data on one or more mispronunciations of a spoken word utterance associated with the specific health condition, the training data on the one or more mispronunciations of the spoken word utterance received through a secure portal provided by a model training engine;

retraining, by the model training engine, the first machine learning model using the training data on the one or more mispronunciations of the spoken word utterance associated with the specific health condition;

retrieving data related to the patient member user, the data including the user input received through the conversational interface application and historical data regarding the specific health condition;

determining a second applicable intent of the patient member user based on the user interaction history, the second applicable intent of the patient member user determined by the first machine learning model retrained to identify the second applicable intent from the one or more mispronunciations of the spoken word utterance received through the secure portal provided by the model training engine;

determining one or more recommended actions to access health care related to the specific health condition based on an output of a second machine learning model selected based on the second applicable intent, the historical data, and the data related to the patient member user, wherein the one or more responses and the user interaction history are used as input to the second machine learning model; and presenting the one or more recommended actions to the patient member user through the conversational interface application.

9. The system of claim 8, wherein the operations further comprise:

retrieving data related to the patient member user, the data including clinical data about the patient member user;

determining a third machine learning model based on the clinical data and the data related to the patient member user; and determining the one or more recommended actions to access healthcare based on the third machine learning model.

10. The system of claim 8, wherein one or more machine learning models are used in determining the applicable intent of the patient member user based on the user input, wherein the one or more machine learning models comprises a trained natural language understanding (NLU) model that classifies user input utterance and one or more of patient member profile, past medical and clinical history, and demographic data.

11. The system of claim 10, wherein the one or more machine learning models comprises at least one of a neural network, support vector machine, a decision tree, a Bayesian network, a random decision forest, a k-nearest neighbor, a linear regression, a least squares, and a hidden Markov model.

12. The system of claim 8, wherein the one or more recommended actions comprises at least one of an in-person office visit, a home visit, a phone call, a video visit, an email, a text, or an instant messaging chat.

13. The system of claim 8, wherein the conversational interface application includes at least one of a digital interface, a self-service interface, a telephony interface, or an interactive voice response (IVR).

14. The system of claim 8, wherein the operations further comprise:

receiving feedback from the patient member user completing the one or more recommended actions; and training one or more machine learning models based on the feedback.

\*   \*   \*   \*   \*